United States Patent
Kwok et al.

(10) Patent No.: US 7,094,555 B2
(45) Date of Patent: Aug. 22, 2006

(54) METHODS OF MHC CLASS II EPITOPE MAPPING, DETECTION OF AUTOIMMUNE T CELLS AND ANTIGENS, AND AUTOIMMUNE TREATMENT

(75) Inventors: William W. Kwok, Bellevue, WA (US); Gerald Nepom, Bainbridge, WA (US); John Gebe, Bothell, WA (US); Helena Reijonen, Seattle, WA (US); Andrew Liu, Seattle, WA (US)

(73) Assignee: Benaroya Research Institute at Virginia Mason, Seattle, WA (US)

( * ) Notice: Subject to any disclaimer, the term of this patent is extended or adjusted under 35 U.S.C. 154(b) by 22 days.

(21) Appl. No.: 10/116,846

(22) Filed: Apr. 5, 2002

(65) Prior Publication Data

US 2003/0073102 A1    Apr. 17, 2003

Related U.S. Application Data

(60) Provisional application No. 60/308,962, filed on Jul. 30, 2001, provisional application No. 60/282,328, filed on Apr. 5, 2001.

(51) Int. Cl.
*G01N 33/53* (2006.01)

(52) U.S. Cl. ............................ 435/7.2; 435/7.1; 435/4; 435/DIG. 3; 435/DIG. 2; 530/388.75; 530/350

(58) Field of Classification Search ................ 435/7.1, 435/7.2, 4, DIG. 3, DIG. 2; 530/388.75, 530/350
See application file for complete search history.

(56) References Cited

U.S. PATENT DOCUMENTS

| 5,635,363 A | 6/1997 | Altman et al. |
| 5,824,315 A | 10/1998 | Nag |
| 6,194,207 B1 | 2/2001 | Bell et al. |
| 6,194,302 B1 | 2/2001 | Shen |
| 6,211,342 B1 | 4/2001 | Hirsch et al. |

FOREIGN PATENT DOCUMENTS

| EP | 0 239 400 A2 | 9/1987 |
| WO | WO 97/35991 | 10/1997 |
| WO | WO98/06749 | 2/1998 |
| WO | WO 99/50637 | 10/1999 |

OTHER PUBLICATIONS

Kunkel et al., "Contact-site cross-linking agents," *Mol. Cell. Biochem.* 34:3-13 (1981).
Marsh, "HLA class II region sequences, 1998," *Tissue Antigens* 51:467-507 (1998).
Altman et al., "Formation of functional peptide complexes of class II major histocompatibility complex protenis from subunits produced in *Escherichia coli*," Proc. Natl. Acad. Sci. USA 90:10330-34 (Nov. 1993).
Altman et al., "Phenotypic Analysis of Antigen-Specific T Lymphocytes," *Science* 274:94-96 (Oct. 4, 1996).
Arimilli et al., "Refolding and Reconstitution of Functionally Active Complexes of Human Leukoycte Antigen DR2 and Myelin Basic Protein Peptide from Recombinant α and β Polypeptide Chains," *J. Biol. Chem.* 270(2):971-977 (Jan. 13, 1995).
Atkinson et al., "Response of peripheral-blood mononuclear cells to glutamate decarboxylase in insulin-dependent diabetes," *Lancet* 339:458-459 (Feb. 22, 1992).
Benjamin and Datta, "Modified Pulse Field Gel Electrophoresis Technique Using Pefabloc® SC for Analyzing *Listeria monocytogenes* DNA," *Biochemica* 2:30-31 (1995).
Blake et al., "The Importance of Exogenous Antigen in Priming the Human $CD8^+$ T Cell Response: Lessons from the EBV Nuclear Antigen EBNA1," *J. Immunol.* 165: 7078-87 (2000).
Brosterhus et al., "Enrichment and detection of live antigen-specific $CD4^+$ and $CD8^+$ T cells based on cytokine secretion," *Eur. J. Immunol.* 29:4053 (1999).
Brusic et al., "MHCPEP, a database of MHC-binding peptides: update 1997," *Nucleic Acids Res.* 26:368-371 (1998).
Brusic et al., "Prediction of MHC class II-binding peptides using an evolutionary algorithm and artificial neural network," *Bioinformatics* 14:121-30 (1998).
Callan et al., "Direct Visualization of Antigen-pecific CD8+ T Cells during the Primary Immune Response to Epstein-Barr Virus in vivo," *J. Exp. Med.* 187:1395-1402 (1998).
Cameron et al., "Cutting Edge: Detection of Antigen-Specific $CD4^+$ T Cells by HLA-DR1 Oligomers is Dependent on the T Cell Activation State," *J. Immunol.* 166:741-745 (2001).
Chang et al., "A general method for facilitating heterodimeric pairing between two proteins: Application to expression of α and β T-cell receptor extracellular segments," *Proc. Natl. Acad. Sci. USA* 91:11408-11412 (1994).

(Continued)

*Primary Examiner*—T. D. Wessendorf
(74) *Attorney, Agent, or Firm*—Townsend and Townsend and Crew LLP

(57) ABSTRACT

The present invention provides of using multimeric MHC class II/peptide complexes. In one aspect, methods provided for identifying MHC class II-restricted immune epitopes of a predetermined polypeptide antigen. Methods for identifying an immunostimulatory epitope for a predetermined polypeptide antigen are provided. In a related aspect, methods for screening a therapeutic polypeptide agent for an MHC class II epitope are provided. In other aspects, methods for modulating T cells and for determining or monitoring an MHC class II-restricted immune status of a patient are also provided.

16 Claims, No Drawings

OTHER PUBLICATIONS

Chang et al., "Identification of HLA-A3 and -B7-Restricted CTL Response to Hepatitis CVirus in Patients with Acute and Chronic Hepatitis C," *J. Immunol.* 162:1156-1164 (1999).

Cochlovius et al., "In Vitro and In Vivo Induction of a Th Cell Response Toward Peptides of the Melanoma-Associated Glycoprotein 100 Protein Selected by the TEPITOPE Program," *J. Immunol.* 165:4731-41 (2000).

Crawford et al., "Detection of Antigen-Specific T Cells with Multivalent Soluble Class II MHC Covalent Peptide Complexes," *Immunity* 8:675-682 (1998).

Cwynarski et al., "Direct visualization of cytomegalovirus-specific T-cell reconstitution after allogeneic stem cell transplantation," *Blood* 97:1232-40 (Mar. 1, 2001).

De Lalla et al., "Cutting Edge: Identification of Novel T Cell Epitopes in Lol p5a by Computational Prediction," *J. Immunol.* 163:1725-29 (1999).

Demotz et al., "The set of naturally processed peptides displayed by DR molecules is tuned by polymorphism of residue 86," *Eur. J. Immunol.* 23:425-32 (1993).

Denkberg et al., "Recombinant human single-chain MHC-peptide complexes made from *E. coli* by *in vitro* refolding: functional single-chain MHC-peptide complexes and tetramers with tumor associated antigens," *Eur. J. Immunol.* 30(12):3522-32 (Dec. 2000).

Dessen et al., "X-Ray Crystal Structure of HLA-DR4 (DRA*0101, DRB1*0401) Complexed with a Peptide from Human Collagen II," *Immunity* 7:473-481 (Oct. 1997).

Dunbar et al., "Cutting Edge: Rapid Cloning of Tumor-Specific CTL Suitable for Adoptive Immunotherapy of Melanoma," *J. Immunol.* 162:6959 (1999).

Endl et al., "Identification of Naturally Processed T Cell Epitopes from Glutamic Acid Decarboxylase Presented in the Context of HLA-DR Alleles by T Lymphocytes of Recent Onset IDDM Patients," *J. Clin. Invest.* 99:2405-15 (May 1997).

Ettinger and Kwok, "A Peptide Binding Motif for HLA-DQA*0102/DQB1*0602, the Class II MHC Molecule Associated with Dominant Protection in Insulin-Dependent Diabetes Mellitus," *J. Immunol.* 160:2365-73 (1998).

Ettinger et al., "Exceptional Stability of the HLA-DQA1*0102/DQB1*0602 αβ Protein Dimer, the Class II MHC Molecule Associated with Protection from Insulin-Dependent Diabetes Mellitus," *J. Immunol.* 161:6439-6445 (1998).

Ettinger et al., "β57-Asp Plays an Essential Role in the Unique SDS Stability of HLA-DQA1*0102/DQB1*0602 αβ Protein Dimer, the Class II MHC Allele Associated with Protection from Insulin-Dependent Diabetes Mellitus," *J. Immunol.* 165:3232-38 (2000).

Falk et al., "Induction and Suppression of an Autoimmune Disease by Oligomerized T Cell Epitopes: Enhanced In Vivo Potency of Encephalitogenic Peptides," *J. Exp. Med.* 191:717-730 (Feb. 21, 2000).

Fraser et al., "Signal transduction events leading to T-cell lymphokine gene expression," *Immunol. Today* 14:357-362 (1993).

Gallimore et al., "Induction and Exhaustion of Lymphocytic Choriomeningitis Virus-specific Cytotoxic T Lymphocytes Visualized Using Soluble Tetrameric Major Histocompatibility Complex Class I-Peptide Complexes," *J. Exp. Med.* 187:1383-1393 (May 4, 1998).

Garboczi et al., "HLA-A2-peptide complexes: Refolding and crystallization of molecules expressed in *Escherichia coli* and complexed with single antigenic peptides," *Proc. Natl. Acad. Sci. USA* 89:3429-33 (Apr. 1992).

Geluk et al., "Identification of Major Epitopes of *Mycobacterium tuberculosis* AG85B That Are Recognized by HLA-A*0201-Restricted CD8+ T Cells in HLA-Transgenic Mice and Humans," *J. Immunol.* 165:6463-71 (2000).

Hammer et al., "Precise Prediction of Major Histocompatibility Complex Class II-Peptide Interaction Based on Peptide Side Chain Scanning," *J. Exp. Med.* 180:2353-58 (Dec. 1994).

Hammer et al., "HLA Class II Peptide Binding Specificity and Autoimmunity," *Adv. Immunol* 66:67-100 (1997).

Honeyman et al., "Neural network-based prediction of candidate T-cell epitopes," *Nat. Biotechnol.* 16:966-69 (Oct. 1998).

Horton et al., "Gene Splicing by Overlap Extension: Tailor-Made Genes Using the Polymerase Chain Reaction," *Biotechniques* 8:528-535 (1990).

Kaufman et al., "Spontaneous loss of T-cell tolerance to glumatic acid decarboxylase in murine insulin-dependent diabetes," *Nature* 366:69-72 (Nov. 4, 1993).

Kern et al., "T cell epitope mapping by flow cytometry," *Nat. Med.* 4:975-978 (Aug. 1998).

Kim et al., "Direct Detection and Magnetic Isolation of *Chlamydia trachomatis* Major Outer Membrane Protein-Specific CD8+ CTLs with HLA Class I Tetramers," *J. Immunol.* 165: 7285-92 (2000).

Klein et al., "HLA-B*35-Restricted CD8 T Cell Epitopes in the Antigen 85 Complex of *Mycobacterium tuberculosis*," *J. Infect. Dis.* 183:928-34 (2001).

Koelle et al., "Recognition of Herpes Simplex Virus Type 2 Tegument Proteins by CD4 T Cells Infiltrating Human Genital Herpes Lesions," *J. Virol.* 72:7476-83 (Sep. 1998).

Konig et al., "The Structural Basis of CD4—MHC Class II Interactions: Coreceptor Contributions to T Cell Receptor Antigen Recognition and Oligomerization-Dependent Signal Transduction," *Curr. Top. Microbiol. Immunol.* 205:19-46 (1996).

Kotzin et al:, "Use of soluble peptide-DR4 tetramers to detect synovial T cells specific for cartilage antigens in patients with rheumatoid arthritis," *Proc. Natl. Acad. Sci. USA* 97:291-296 (Jan. 4, 2000).

Kovats et al., "Deficient Antigen-presenting Cell Function in Multiple Genetic Complementation Groups of Type II Bare Lymphocyte Syndrome," *J. Clin. Invest.* 96:217-223 (1995).

Kwok et al., "HLA-DQ Tetramers Identify Epitope-Specific T cells in Peripheral Blood of Herpes Simplex Virus Type 2-Infected Individuals: Direct Detection of Immunodominant Antigen-Responsive Cells," *J. Immunology* 164:4244-49 (2000).

Kwok et al., "HLA-DQ Tetramers Identify Epitope-Specific T Cells in Peripheral Blood of Herpes Simplex Virus-2 (HSV-2)-Infected Individuals: Direct Detection of Antigen Responsive Cells," Abstract published in *The FASEB Journal*, The American Association of Immunologists and the Clinical Immunology Society Joint Annual Meeting (Immunolgy 2000), Seattle, WA (May 12-16, 2000).

Kwok et al., "Direct Identification of T Cell Epitopes Using HLA-Class II Tetramers," Abstract published in *The FASEB Journal*, The American Association of Immunologists and the Clinical Immunology Society Joint Annual Meeting (Immunolgy 2000), Seattle, WA (May 12-16, 2000).

Kwok et al., "Rapid epitope identification from complex class-II-restricted T-cell antigens," *Trends in Immunol.* 22:583-8 (Nov. 2001).

Lee et al., "Characterization of circulating T cells specific for tumor-associated antigens in melanoma patients," *Nat. Med.* 5:677 (Jun. 1999).

Liu et al., "Detection of glutamic acid decarboxylase-activated T cells with I-A$^{g7}$ tetramers," *Proc. Natl. Acad. Sci. USA* 97:14596-601 (Dec. 19, 2000).

Manici et al., "Melanoma Cells Present a MAGE-3 Epitope to CD4+ Cytotoxic T Cells in Association with Histocompatibility Leukocyte Antigen DR11," *J Exp. Med.* 189:871-76 (1999).

Marshall et al., "Prediction of Peptide Affinity to HLA DRB1*0401," *J. Immunol.* 154:5927-33 (1995).

Masewicz et al., "Complexity of Human Immune response Profiles for CD4+T Cell Epitopes from the Diabetes Autoantigen GAD65," *Autoimmunity* 34:231-240 (2001).

Meyer et al., "Direct enumeration of *Borrelia*-reactive CD4 T cells ex vivo by using MHC class II tetramers," *Proc. Natl. Acad. Sci. USA* 97:11433-38 (2000).

Michaelsson et al., "Macrophages, but not dendritic cells, present collagen to T cells," *Eur. J. Immunol.* 25: 2234-2241 (1995).

Molldrem et al., "A PRI-Human Leukocyte Antigen-A2 Tetramer Can Be Used to Isolate Low-Frequency Cytotoxic T Lymphocytes from Healthy Donors That Selectively Lyse Chronic Myelogenous Leukemia," *Cancer Res.* 59:2675 (Jun. 1, 1999).

Nepom et al., "Identification and modulation of a naturally processed T cell epitope from the diabetes-associated autoantigen human glutamic acid decarboxylase 65 (hGAD65)," *Proc. Natl. Acad. Sci. USA* 98:1763-68 (2001).

Novak et al., "MHC class II tetramers identify peptide-specific human CD4+ T cells proliferating in response to influenza A antigen," *J. Clin. Invest.* 104:R63-67 (1999).

Novak et al., "Tetramer-Guided Epitope Mapping: Rapid Identification and Characterization of Immunodominant CD4+ T Cell Epitopes from Complex Antigens," *J. Immunol.* 166:6665-70 (2001).

Novak et al., "Activated human epitope-specific T cells identified by class II tetramers reside within a $CD4^{high}$, proliferating subset," *Int. Immunol.* 13:799-806 (Mar. 5, 2001).

Ovsyannikova et al., "Isolation and rapid identification of an abundant self-peptide from class II HLA-DRB1*0401 alleles induced by measles vaccine virus infection," *J. Immunol. Methods* 246:1-12 (Dec. 2000).

Panina-Bordignon et al.,"Cytotoxic T Cells Specific for Glutamic Acid Decarboxylase in Autoimmune Diabetes," *J. Exp. Med.* 181:1923-27 (1995).

Patel et al., "Identification of immunodominant T cell epitopes of human glutamic acid decarboxylase 65 by using HLA-DR($\alpha$1*0101,$\beta$ 1*0401) transgenic mice," *Proc. Natl. Acad. Sci. USA* 94:8082-87 (Jul. 1997).

Pittet et al., "High Frequencies of Naive Melan-A/MART-1-specific $CD8^+$T Cells in a Large Proportion of Human Histocompatibility Leukocyte Antigen (HLA)-A2 Individuals," *J. Exp. Med.* 190:705-715 (Sep. 6, 1999).

Prezzi et al., "Virus-specific $CD8^+$ T cells with type 1 or type 2 cytokine profile are related to different disease activity in chronic hepatitis C virus infection," *Eur. J. Immunol.* 31:894-906 (2001).

Qu and Green, "Folding and Assembly of a Human MHC Class II Molecule in a Cell-Free System," *DNA Cell Biol.* 14:741-51 (1995).

Rammensee et al., "SYFPEITHI: database for MHC ligands and peptide motifs," *Immunogenet.* 50:213-19 (1999).

Rammensee et al. "MHC ligands and peptide motifs: first listing," *Immunogenet.* 41:178-228 (1995).

Reichstetter et al., "Distinct T Cell Interactions with HLA Class II Tetramers Characterize a Spectrum of TCR Affinities in the Human Antigen-Specific T Cell Response," *J. Immunol.* 165:6994-6998 (2000).

Reijonen et al., "Differential Presentation of Glutamic Acid Decarboxylase (GAD65) T Cell Epitopes Among HLA-DRB1*0401-Positive Individuals," *J. Immunol.* 163:1674-1681 (1999).

Reijonen et al., "Detection of GAD65-Specific T-Cells by Major Histocompatibility Complex Class II Tetramers in Type 1 Diabetic Patients and At-Risk Subjects," *Diabetes* 51:1375-82 (May 2002).

Ridgway et al., "Following Antigen Challenge, T Cells Up-Regulate Cell Surface Expression of CD4 In Vitro and In Vivo," *J Immunol.* 161:714-20 (1998).

Rolland and O'Hehir, "Immunotherapy of allergy: anergy, deletion, and immune deviation," *Curr. Opin. Immunol.* 10:640-645 (1998).

Roy et al., "Induction of antigen-specific CD8+ T cells, T helper cells, and protective levels of antibody in humans by particle-mediated administration of a hepatitis B virus DNA vaccine," *Vaccine* 19:764-78 (2000).

Schatz, "Use of Peptide Libraries to Map the Substrate Specificity of a Peptide-Modifying Enzyme: A 13 Residue Consensus Peptide Specifies Biotinylation in *Escherichia coli*," *Biotechnology* 11:1138-1143 (Oct. 1993).

Schneider and Sercarz, "Antigen Processing Differences Among APC," *Human Immunol.* 54:148-158 (1997).

Sette et al., "HLA DR4w4-Binding Motifs Illustrate the Biochemical Basis of Degeneracy and Specificity in Peptide-DR Interactions," *J. Immunol.* 151:3163-3170 (Sep. 15, 1993).

Southwood et al., "Several Common HLA-DR Types Share Largely Overlapping Peptide Binding Repertoires,"*J. Immunol.* 160:3363-73 (1998).

Stern and Wiley, "The Human Class II MHC Protein HLA-DR1 Assembles as Empty $\alpha\beta$ Heterodimers in the Absence of Antigenic Peptide," *Cell* 68:465-77 (Feb. 7, 1992).

Sturniolo et al., "Generation of tissue-specific and promiscuous HLA ligand databases using DNA microarrays and virtual HLA class II matrices," *Nat. Biotechnol.* 17:555-61 (Jun. 1999).

Tisch et al., "Immune response to glutamic acid decarboxylase correlates with insulitis in non-obese diabetic mice," *Nature* 366:72-75 (Nov. 4, 1993).

Van Neerven et al., "T-cell responses to allergens: epitope-specificity and clinical relevance," *Immunol. Today* 17(11):526-32 (Nov. 1996).

Vidard et al., "Heterogeneity in Antigen Processing by Different Types of Antigen-Presenting Cells: Effect of Cell Culture on Antigen Processing Ability," *J. Immunol.* 149:1905-1911 (Sep. 15, 1992).

Wang and Rosenberg, "Human tumor antigens for cancer vaccine development," *Immunol. Rev.* 170:85-100 (1999).

Wen et al., "Induction of Insulitis by Glutamic Acid Decarboxylase Peptide-specific and HLA-DQ8-restricted CD4+ T Cells from Human DQ Transgenic Mice," *J. Clin. Invest.* 102:947-57 (Sep. 1998).

Wicker et al., "Naturally Processed T cell Epitopes from Human Glutamic Acid Decarboxylase Identified Using Mice Transgenic for the Type I Diabetes-associated Human MHC Class II Allele, DRB1*0401," *J. Clin. Invest.* 98:2597-603 (Dec. 1996).

Wilson et al., "Oligoclonal Expansions of $CD8^+$ T Cells in Chronic HIV Infection Are Antigen Specific," *J. Exp. Med.* 188:785-790 (Aug. 17, 1998).

Yoon et al., "Control of Autoimmune Diabetes in NOD Mice by GAD Expression or Suppression in $\beta$ Cells," *Science* 284:1183-87 (May 14, 1999).

SEQUENCE LISTING

```
<160> NUMBER OF SEQ ID NOS: 49

<210> SEQ ID NO 1
<211> LENGTH: 11
<212> TYPE: PRT
<213> ORGANISM: Herpes Simplex Virus 2

<400> SEQUENCE: 1

Pro Met Pro Val Pro Pro Ala Ala Leu Phe Asn
1               5                   10

<210> SEQ ID NO 2
<211> LENGTH: 13
<212> TYPE: PRT
<213> ORGANISM: Herpes Simplex Virus 2

<400> SEQUENCE: 2

Thr Asp Val Ser Leu Gly Asp Glu Leu Arg Leu Asp Gly
1               5                   10

<210> SEQ ID NO 3
<211> LENGTH: 12
<212> TYPE: PRT
<213> ORGANISM: Herpes Simplex Virus 2

<400> SEQUENCE: 3

Ala Leu Phe Asn Arg Leu Leu Asp Asp Leu Gly Phe
1               5                   10

<210> SEQ ID NO 4
<211> LENGTH: 13
<212> TYPE: PRT
<213> ORGANISM: Herpes Simplex Virus 2

<400> SEQUENCE: 4

Asp Phe Glu Phe Glu Gln Met Phe Thr Asp Ala Met Gly
1               5                   10

<210> SEQ ID NO 5
<211> LENGTH: 13
<212> TYPE: PRT
<213> ORGANISM: Herpes Simplex Virus 2

<400> SEQUENCE: 5

Phe Asp Leu Glu Met Leu Gly Asp Val Glu Ser Pro Ser
1               5                   10

<210> SEQ ID NO 6
<211> LENGTH: 9
<212> TYPE: PRT
<213> ORGANISM: Herpes Simplex Virus 2

<400> SEQUENCE: 6

Tyr Arg Thr Val Leu Ala Asn Phe Cys
1               5

<210> SEQ ID NO 7
```

```
<211> LENGTH: 9
<212> TYPE: PRT
<213> ORGANISM: Herpes Simplex Virus 2

<400> SEQUENCE: 7

Val Leu Ala Asn Phe Cys Ser Ala Leu
1               5

<210> SEQ ID NO 8
<211> LENGTH: 9
<212> TYPE: PRT
<213> ORGANISM: Herpes Simplex Virus 2

<400> SEQUENCE: 8

Tyr Arg Tyr Leu Arg Ala Ser Val Arg
1               5

<210> SEQ ID NO 9
<211> LENGTH: 9
<212> TYPE: PRT
<213> ORGANISM: Herpes Simplex Virus 2

<400> SEQUENCE: 9

Tyr Leu Arg Ala Ser Val Arg Gln Leu
1               5

<210> SEQ ID NO 10
<211> LENGTH: 9
<212> TYPE: PRT
<213> ORGANISM: Herpes Simplex Virus 2

<400> SEQUENCE: 10

Tyr Tyr Arg Glu Thr Ala Arg Leu Ala
1               5

<210> SEQ ID NO 11
<211> LENGTH: 9
<212> TYPE: PRT
<213> ORGANISM: Herpes Simplex Virus 2

<400> SEQUENCE: 11

Leu Tyr Leu Phe Leu Ser Arg Glu Ile
1               5

<210> SEQ ID NO 12
<211> LENGTH: 9
<212> TYPE: PRT
<213> ORGANISM: Herpes Simplex Virus 2

<400> SEQUENCE: 12

Tyr Leu Phe Leu Ser Arg Glu Ile Leu
1               5

<210> SEQ ID NO 13
<211> LENGTH: 9
<212> TYPE: PRT
<213> ORGANISM: Herpes Simplex Virus 2

<400> SEQUENCE: 13

Trp Arg Gln Leu Ala Cys Leu Phe Gln
1               5

<210> SEQ ID NO 14
<211> LENGTH: 9
<212> TYPE: PRT
```

<213> ORGANISM: Herpes Simplex Virus 2

<400> SEQUENCE: 14

Leu Met Phe Ile Asn Gly Ser Leu Thr
1               5

<210> SEQ ID NO 15
<211> LENGTH: 9
<212> TYPE: PRT
<213> ORGANISM: Herpes Simplex Virus 2

<400> SEQUENCE: 15

Met Phe Ile Asn Gly Ser Leu Thr Val
1               5

<210> SEQ ID NO 16
<211> LENGTH: 9
<212> TYPE: PRT
<213> ORGANISM: Herpes Simplex Virus 2

<400> SEQUENCE: 16

Leu Gln Gly Asn Gln Ala Arg Ser Ser
1               5

<210> SEQ ID NO 17
<211> LENGTH: 9
<212> TYPE: PRT
<213> ORGANISM: Herpes Simplex Virus 2

<400> SEQUENCE: 17

Phe Met Leu Leu Ile Arg Ala Lys Leu
1               5

<210> SEQ ID NO 18
<211> LENGTH: 9
<212> TYPE: PRT
<213> ORGANISM: Herpes Simplex Virus 2

<400> SEQUENCE: 18

Ile Asn Gly Ser Leu Thr Val Arg Gly
1               5

<210> SEQ ID NO 19
<211> LENGTH: 9
<212> TYPE: PRT
<213> ORGANISM: Herpes Simplex Virus 2

<400> SEQUENCE: 19

Ile Arg Glu His Leu Asn Leu Pro Leu
1               5

<210> SEQ ID NO 20
<211> LENGTH: 9
<212> TYPE: PRT
<213> ORGANISM: Herpes Simplex Virus 2

<400> SEQUENCE: 20

Phe Glu Gln Met Phe Thr Asp Ala Met
1               5

<210> SEQ ID NO 21
<211> LENGTH: 9
<212> TYPE: PRT
<213> ORGANISM: Herpes Simplex Virus 2

```
<400> SEQUENCE: 21

Phe Leu Ser Arg Glu Ile Leu Trp Ala
1               5

<210> SEQ ID NO 22
<211> LENGTH: 9
<212> TYPE: PRT
<213> ORGANISM: Herpes Simplex Virus 2

<400> SEQUENCE: 22

Leu Asn Leu Pro Leu Val Arg Ser Ala
1               5

<210> SEQ ID NO 23
<211> LENGTH: 9
<212> TYPE: PRT
<213> ORGANISM: Herpes Simplex Virus 2

<400> SEQUENCE: 23

Tyr Phe Met Leu Leu Ile Arg Ala Lys
1               5

<210> SEQ ID NO 24
<211> LENGTH: 9
<212> TYPE: PRT
<213> ORGANISM: Herpes Simplex Virus 2

<400> SEQUENCE: 24

Leu Leu Ile Arg Ala Lys Leu Asp Ser
1               5

<210> SEQ ID NO 25
<211> LENGTH: 9
<212> TYPE: PRT
<213> ORGANISM: Herpes Simplex Virus 2

<400> SEQUENCE: 25

Val Ala Pro Arg Met Ser Phe Leu Ser
1               5

<210> SEQ ID NO 26
<211> LENGTH: 8
<212> TYPE: PRT
<213> ORGANISM: Herpes Simplex Virus 2

<400> SEQUENCE: 26

Arg Gly Val Pro Val Glu Ala Arg
1               5

<210> SEQ ID NO 27
<211> LENGTH: 9
<212> TYPE: PRT
<213> ORGANISM: Herpes Simplex Virus 2

<400> SEQUENCE: 27

Leu Pro Leu Val Arg Ser Ala Ala Ala
1               5

<210> SEQ ID NO 28
<211> LENGTH: 9
<212> TYPE: PRT
<213> ORGANISM: Herpes Simplex Virus 2

<400> SEQUENCE: 28
```

```
Leu Glu Met Leu Gly Asp Val Glu Ser
1               5

<210> SEQ ID NO 29
<211> LENGTH: 9
<212> TYPE: PRT
<213> ORGANISM: Herpes Simplex Virus 2

<400> SEQUENCE: 29

Leu Tyr Ala Thr Gly Arg Leu Ser Gln
1               5

<210> SEQ ID NO 30
<211> LENGTH: 9
<212> TYPE: PRT
<213> ORGANISM: Herpes Simplex Virus 2

<400> SEQUENCE: 30

Val Arg Gln Leu His Arg Gln Ala His
1               5

<210> SEQ ID NO 31
<211> LENGTH: 9
<212> TYPE: PRT
<213> ORGANISM: Herpes Simplex Virus 2

<400> SEQUENCE: 31

Phe Leu His Leu Tyr Leu Phe Leu Ser
1               5

<210> SEQ ID NO 32
<211> LENGTH: 9
<212> TYPE: PRT
<213> ORGANISM: Herpes Simplex Virus 2

<400> SEQUENCE: 32

Met Ala Gln Phe Phe Arg Gly Glu Leu
1               5

<210> SEQ ID NO 33
<211> LENGTH: 9
<212> TYPE: PRT
<213> ORGANISM: Herpes Simplex Virus 2

<400> SEQUENCE: 33

Leu Tyr Arg Tyr Leu Arg Ala Ser Val
1               5

<210> SEQ ID NO 34
<211> LENGTH: 9
<212> TYPE: PRT
<213> ORGANISM: Herpes Simplex Virus 2

<400> SEQUENCE: 34

Leu Arg Glu Met Leu Arg Thr Thr Ile
1               5

<210> SEQ ID NO 35
<211> LENGTH: 9
<212> TYPE: PRT
<213> ORGANISM: Herpes Simplex Virus 2

<400> SEQUENCE: 35

Leu Phe Leu His Leu Tyr Leu Phe Leu
1               5
```

```
<210> SEQ ID NO 36
<211> LENGTH: 9
<212> TYPE: PRT
<213> ORGANISM: Herpes Simplex Virus 2

<400> SEQUENCE: 36

Leu His Leu Tyr Leu Phe Leu Ser Arg
1               5

<210> SEQ ID NO 37
<211> LENGTH: 20
<212> TYPE: PRT
<213> ORGANISM: Herpes Simplex Virus 2

<400> SEQUENCE: 37

Ile Ala Asp Arg Tyr Tyr Arg Glu Thr Ala Arg Leu Ala Arg Val Leu
1               5                   10                  15

Phe Leu His Leu
            20

<210> SEQ ID NO 38
<211> LENGTH: 12
<212> TYPE: PRT
<213> ORGANISM: Herpes Simplex Virus 2

<400> SEQUENCE: 38

Ala Leu Phe Asn Arg Leu Leu Asp Asp Leu Gly Phe
1               5                   10

<210> SEQ ID NO 39
<211> LENGTH: 20
<212> TYPE: PRT
<213> ORGANISM: Herpes Simplex Virus 2

<400> SEQUENCE: 39

Pro Ala Leu Cys Thr Met Leu Asp Thr Trp Asn Glu Asp Leu Phe Ser
1               5                   10                  15

Gly Phe Pro Thr
            20

<210> SEQ ID NO 40
<211> LENGTH: 20
<212> TYPE: PRT
<213> ORGANISM: Herpes Simplex Virus 2

<400> SEQUENCE: 40

Ser Arg Glu Ile Leu Trp Ala Ala Tyr Ala Glu Gln Met Met Arg Pro
1               5                   10                  15

Asp Leu Phe Asp
            20

<210> SEQ ID NO 41
<211> LENGTH: 13
<212> TYPE: PRT
<213> ORGANISM: Herpes Simplex Virus 2

<400> SEQUENCE: 41

Asp Phe Glu Phe Glu Gln Met Phe Thr Asp Ala Met Gly
1               5                   10

<210> SEQ ID NO 42
<211> LENGTH: 20
```

```
<212> TYPE: PRT
<213> ORGANISM: Herpes Simplex Virus 2

<400> SEQUENCE: 42

Arg Leu Arg Glu Leu Asn His Ile Arg Glu His Leu Asn Leu Pro Leu
1               5                   10                  15

Val Arg Ser Ala
            20

<210> SEQ ID NO 43
<211> LENGTH: 20
<212> TYPE: PRT
<213> ORGANISM: Herpes Simplex Virus 2

<400> SEQUENCE: 43

Asp Asp Ala Pro Ala Glu Ala Gly Leu Val Ala Pro Arg Met Ser Phe
1               5                   10                  15

Leu Ser Ala Gly
            20

<210> SEQ ID NO 44
<211> LENGTH: 20
<212> TYPE: PRT
<213> ORGANISM: Herpes Simplex Virus 2

<400> SEQUENCE: 44

Phe Leu His Leu Tyr Leu Phe Leu Ser Arg Glu Ile Leu Trp Ala Ala
1               5                   10                  15

Tyr Ala Glu Gln
            20

<210> SEQ ID NO 45
<211> LENGTH: 13
<212> TYPE: PRT
<213> ORGANISM: Herpes Simplex Virus 2

<400> SEQUENCE: 45

Phe Asp Leu Glu Met Leu Gly Asp Val Glu Ser Pro Ser
1               5                   10

<210> SEQ ID NO 46
<211> LENGTH: 20
<212> TYPE: PRT
<213> ORGANISM: Herpes Simplex Virus 2

<400> SEQUENCE: 46

Gly Pro Lys Asn Thr Pro Ala Ala Pro Pro Leu Tyr Ala Thr Gly Arg
1               5                   10                  15

Leu Ser Gln Ala
            20

<210> SEQ ID NO 47
<211> LENGTH: 20
<212> TYPE: PRT
<213> ORGANISM: Herpes Simplex Virus 2

<400> SEQUENCE: 47

Pro Pro Leu Tyr Ala Thr Gly Arg Leu Ser Gln Ala Gln Leu Met Pro
1               5                   10                  15

Ser Pro Pro Met
            20
```

```
-continued

<210> SEQ ID NO 48
<211> LENGTH: 13
<212> TYPE: PRT
<213> ORGANISM: Homo sapien

<400> SEQUENCE: 48

Asn Phe Ile Arg Met Val Ile Ser Asn Pro Ala Ala Thr
1               5                   10

<210> SEQ ID NO 49
<211> LENGTH: 18
<212> TYPE: PRT
<213> ORGANISM: Homo sapiens

<400> SEQUENCE: 49

Asn Pro Val Val His Phe Phe Lys Asn Ile Val Thr Pro Arg Thr Pro
1               5                   10                  15

Pro Pro
```

METHODS OF MHC CLASS II EPITOPE MAPPING, DETECTION OF AUTOIMMUNE T CELLS AND ANTIGENS, AND AUTOIMMUNE TREATMENT

CONTINUITY

This application claims the benefit of U.S. Provisional Patent Application No. 60/282,328, filed Apr. 5, 2001, and No. 60/308,962, filed Jul. 30, 2001, the disclosures of which are incorporated by reference herein.

STATEMENT AS TO RIGHTS TO INVENTIONS MADE UNDER FEDERALLY SPONSORED RESEARCH AND DEVELOPMENT

This work was supported by U.S. Government grant numbers AI-44443 and AI-30731, awarded by the National Institutes of Health. The U.S. Government may have certain rights in the invention.

BACKGROUND OF THE INVENTION

The T cell-mediated response to complex antigens involves recognition of selected peptide epitopes presented in the context of MHC molecules expressed on antigen presenting cells. The choice of these immunogenic epitopes from among the often hundreds or thousands of amino acids comprising an antigenic protein depends significantly on the binding properties of a given MHC type and the interactions of specific amino acids with a T cell receptor. Understanding which peptide epitopes participate in T cell-mediated immunity provides a basis for directed modulation of the immune response, including development of peptide vaccines and therapies against allergens, autoimmune diseases and tumors. (See, e.g., Chang et al., *J. Immunol.* 162:1156 (1999); Rolland and O'Hehir, *Curr. Opin. Immunol.* 10:640 (1998); Wicker et al., *J. Clin. Invest.* 98:2597 (1996); Falk et al., *J. Exp. Med.* 191:717 (2000); Wang and Rosenberg, *Immunol. Rev.* 170:85 (1999).)

The standard approach for cloning T cells and mapping epitopes of an antigen involves antigen challenge of peripheral blood mononuclear cells (PBMC) followed by plating individual cells into 96-well plates. Cells are then expanded and assayed for MHC restriction and peptide specificities by screening clones with individual peptides which cover the antigen, a labor intensive and time consuming process. Epitopes can also be identified using a combination of chromatography and mass spectroscopy to identify peptides bound to MHC molecules, an approach which requires purification of MHC molecules and coupling to a receptor. Alternatively, epitopes can be identified using a recently described flow cytometry-based approach that utilizes Interferon gamma (IFNγ) production as a marker of reactivity. While this approach simplifies isolation of epitope-specific clones, the task of identifying individual MHC restriction elements remains.

A number of recent studies have employed soluble MHC multimers to directly identify T cells restricted to specific peptide epitopes. This technology has been utilized to track T cells specific for both viral antigens (see, e.g., Altman et al., *Science* 274:94 (1996); Callan et al., *J. Exp. Med.* 187:1395 (1998); Gallimore et al., *J. Exp. Med.* 187:1383 (1998); Wilson et al., *J. Exp. Med.* 188:785 (1998)) and tumor antigens (Lee et al., *Nat. Med.* 5:677 (1999); Pittet et al., *J. Exp. Med.* 190:705 (1999); Dunbar et al., *J. Immunol.* 162:6959 (1999); Molldrem et al., *Cancer Res.* 59:2675 (1999)) in both animal models and in humans when the peptide epitope is known.

The majority of these studies have focused on class I restricted T cells, because efforts in producing MHC class II molecules are hampered by difficulties in generating stable soluble forms of the MHC class II molecules and inefficiency in forming multimers of these molecules. In particular, stable soluble MHC class II molecules bound to peptide have been difficult to form from human MHC class II molecules. Human MHC class II molecules have been difficult to load with peptide, and the resulting multimers can be unstable.

A related problem with using MHC class II molecules to identify epitopes in antigens is that peptides are screened individually to identify the epitope(s) of the antigen. Thus, elucidation of specific epitopes from complex antigens can be a cumbersome and difficult process as it generally involves extensive phenotype screening of T cell clones isolated from whole-antigen stimulated cells.

Thus, there is a need for methods for efficiently screening human T cells to identify MHC class II epitopes within an antigen. The present invention satisfies this and other needs.

BRIEF SUMMARY OF THE INVENTION

The present invention provides methods of using multimeric MHC class II/peptide complexes. In one aspect, methods are provided for identifying MHC class II epitopes of a predetermined polypeptide antigen. The methods generally include preparing a library of at least two peptide pools, each peptide pool comprising at least two peptides. The peptides comprise a fragment of the predetermined polypeptide antigen and share a region of contiguous amino acid sequence identity with at least one other peptide in the library. Soluble human MHC class II molecules are loaded with the peptide pools and formed into pools of multimeric MHC class II/peptide complexes pools. The pools of multimeric MHC class II/peptide complexes are contacted with human T cells to identify at least one pool of multimeric MHC class II/peptide complexes that bind the T cells (e.g., in an epitope-specific manner). The T cells can be isolated, for example, as peripheral blood mononuclear cells. Binding of the complexes to the T cells can be detected, for example, by fluorescence activated cell sorting, by T cell activation assay, or by other suitable method. In some embodiments, the detected T cells can be collected, and optionally can be cultured in vitro to increase the number of T cells. In one embodiment, the cultured T cells are administered to a human subject.

The methods can further include contacting T cells with multimeric MHC class II/peptide complexes formed with individual peptides from a pool of multimeric MHC class II/peptide complexes that bind T cells to identify an MHC class II epitope in the peptide pool. In one embodiment, the identification of a pool(s) of multimeric MHC class II/peptide complexes that binds the T cells is confirmed by T cell activation assay (e.g., proliferation assay or cytokine secretion capture assay; the cytokine secretion capture assay can employ, for example, IFNgamma.)

In certain embodiments, the MHC class II molecules can be loaded by contacting soluble MHC class II molecules with about a 10 to about a 25 fold molar excess of the peptide pools. The peptides can be, for example, about 10 to about 20 amino acids in length. In some embodiments, the overlapping peptides can share about 5 to about 20 amino acids of contiguous sequence identity. Each peptide pool can comprise, for example, about 1, about 3 to about 8 different peptides, or about 5 different peptides.

The soluble human MHC class II molecules can be formed of separate α and β subunits, the α subunits being, for example, HLA-DPα, HLA-DPα or HLA-DRα, and the β subunits being HLA-DPβ, HLA-DQβ or HLA-DRβ. The soluble MHC class II molecules can further comprise α and β subunits, each subunit having a leucine zipper domain or a ligand, whereby the multimeric MHC class II/peptide complexes are formed by interaction of the leucine zipper domains or the ligand with a polyvalent binding partner. Suitable polyvalent binding partners include, for example, streptavidin. The binding partner can optionally be labeled with, for example, a radioactive molecule, a luminescent molecule, a fluorescent molecule, an enzyme, biotin, and the like. In some embodiments, the label is attached to the binding partner by a spacer or flexible linker.

In another aspect, methods are provided for identifying an immunostimulatory epitope for a predetermined polypeptide antigen are provided. The methods generally include preparing pools of peptides, each peptide comprising a fragment of the predetermined polypeptide antigen and having a region of sequence identity with another peptide. A first library of pools of multimeric MHC class II/peptide complexes is formed from the pools of peptides and MHC class II molecules. The first library is contacted with T cells from a human subject to identify at least one pool of multimeric MHC class II/peptide complexes in the first library that binds the T cells. A second library of multimeric MHC class II/peptide complexes can optionally be formed from the individual peptides of the pool(s) of multimeric MHC class II/peptide complexes of the first library that bind the T cells. By analyzing the first and/or second libraries, at least one epitope of the predetermined antigen can be identified.

In one embodiment, the soluble human MHC class II molecules are selected according to the MHC class II molecules of a human subject. In another embodiment, the method further includes forming an immunogenic composition comprising at least one peptide comprising the identified epitope. The multimeric MHC class II/peptide complexes can be, for example, tetramers. The identified epitope can be used to stimulate the proliferation of T cells in vivo or in vitro.

Methods for identifying MHC class II epitopes of the proteome of an organism are also provided. The methods generally include obtaining amino acid sequences for proteins of the organism and analyzing the amino acid sequences with a computer-implemented algorithm for candidate MHC class II epitope identification to identify candidate epitopes. Peptides or pools of peptides, are prepared that contain the candidate epitopes. For example, a first library of pools of multimeric MHC class II/peptide complexes is prepared from the pools of peptides and MHC class II molecules. The multimeric MHC class II/peptide complexes are contacted with T cells to identify at least one pool of multimeric MHC class II/peptide complexes in the first library that bind the T cells. In certain embodiments, a second library of multimeric MHC class II/peptide complexes optionally can be formed using the individual peptides of pools of multimeric MHC class II/peptide complexes of the first library that bind to the T cells. MHC class II epitopes in the proteome of the organism can be identified by analyzing the peptides in the first and/or second peptide libraries that stimulate binding (e.g., epitope-specific binding) of the complexes to T cells.

In certain embodiments, the amino acid sequences can be determined from a database. Such databases can include, for example, a genomic database, a cDNA database, a proteomic database, a compilation of open reading frames, and the like. In another embodiment, the MHC class II molecules can be selected according to the MHC class II molecules of a subject (e.g., a human subject). The multimeric MHC class II/peptide complexes can be, for example, tetramers. The MHC class II epitope, in association with MHC class II molecules can, for example, stimulate the proliferation of T cells. In another embodiment, the computer-implemented algorithm for candidate epitope identification can be the TEPITOPE program. The pools of peptides can optionally be prepared, for example, by automated protein synthesis.

In a related aspect, methods for screening a therapeutic polypeptide agent for an MHC class II epitope are provided. The methods generally include preparing pools of peptides, each peptide comprising a fragment of the polypeptide agent and having a region of sequence identity with another peptide fragment of the polypeptide agent. Typically, each pool has at least one, or at least two, peptide(s). A first library of pools of multimeric MHC class II/peptide complexes is formed with the peptide pools and soluble human MHC class II molecules. The first library is contacted with T cells from a human subject to determine whether the pools of multimeric MHC class II/peptide complexes bind to the T cells, and to determine whether the polypeptide agent has a MHC class II epitope. The soluble human MHC class II molecules can be selected according to the MHC class II molecules of the human subject. The multimeric MHC class II/peptide complexes can be tetramers.

Methods for modulating the state of T cells are also provided. The methods generally include contacting a population of T cells with a multimeric MHC class II/peptide complex conjugated to a biologically active modulatory molecule, and modulating the state of at least one T cell in the population. The multimeric MHC class II/peptide complex confers selective binding and targeting of the biologically active modulatory molecule to the T cells. In various embodiments, the change in state of the T cell can be, for example, apoptosis, anergy, activation, proliferation, or deviation towards alternative cytokine production, as compared with a T cell not contacted with the biologically active modulatory molecule.

The multimeric MHC class II/peptide complexes can confer selective (e.g., epitope-specific) binding and targeting of the biologically active modulatory molecule to the T cells. The biologically active modulatory molecule can be antibody, cytotoxin or other molecule. For example, suitable antibodies can be anti-CD95 antibody, co-stimulatory anti-CTLA4 antibody or co-stimulatory anti-CD28 antibody.

The biologically active modulatory molecules can be coupled to a substrate, such as, for example, a microbead or a polymer. The multimeric complexes can be bound to anti-class II antibodies coupled to the microbead. Alternatively, the multimeric complexes are directly coupled to the bead. In certain embodiments, the multimeric MHC class II/peptide complexes conjugated to the biologically active modulatory molecules can be contacted with T cells ex vivo or in vivo in a human subject.

Methods are also provided for monitoring an MHC class II-restricted immune status of a patient. Such methods generally include isolating T cells from the patient and contacting the T cells with multimeric MHC class II/peptide complexes comprising soluble MHC class II molecules and peptides comprising at least one epitope of interest. The T cells are contacted with the multimeric MHC class II/peptide complexes to determine whether the T cell bind the complexes (e.g., determining whether the T cells are activated by the multimeric MHC class II/peptide complexes). In some embodiments, the patient has an autoimmune disease (e.g., Type 1 diabetes), a hyperproliferative disease, or other disease, and can be receiving a therapeutic agent to treat the disease.

The efficacy or effectiveness of the therapeutic agent can be determined by determining an increase or decrease in T cells that are identified by the multimeric MHC class II/peptide complexes of interest. The increase or decrease in specifically identified T cells can be correlated with the efficacy or effectiveness of the therapeutic agent. The T cells are optionally cultured in vitro and stimulated with a peptide or polypeptide comprising the epitope before contacting the T cells with the multimeric MHC class II/peptide complexes.

DESCRIPTION OF THE SPECIFIC EMBODIMENTS

The present invention provides methods of making and using multimeric MHC class II/peptide complexes. In one aspect, the methods are provided for identifying MHC class II-restricted epitopes of a predetermined polypeptide antigen. The term "epitope", in the context of MHC class II molecules, includes any protein determinant capable of specific binding to a T cell receptor in association with MHC class II molecules. Epitope determinants usually are chemically active surface groupings of molecules such as amino acids or sugar side chains and usually have specific three dimensional structural characteristics, as well as specific charge characteristics.

The methods of identifying epitopes in polypeptide antigens generally include loading soluble human MHC class II molecules with pools of peptides and forming multimeric MHC class II/peptide pairs. The peptides typically represent overlapping fragments of a predetermined antigen. The MHC class II molecules are formed into multimeric MHC class II complexes before or after loading with peptide. The resulting multimeric MHC class II/peptide complexes are contacted with T cells, such as peripheral blood mononuclear cells (PBMC), to identify peptides that have an MHC class II epitope(s) of the predetermined polypeptide antigen.

In another aspect, methods are provided for identifying the epitopes of a predetermined antigen for an individual subject of a known HLA class II genotype. Such methods generally include loading soluble human MHC class II molecules with pools of peptides, the peptides comprising overlapping fragments of the predetermined antigen. The soluble human MHC class II molecules can be selected according to the HLA class II genotype of the individual subject. The MHC class II molecules are formed into MHC class II multimers. The resulting multimeric MHC class II/peptide complexes are contacted with T cells (e.g., PBMC) to identify the MHC class II epitope(s) of the antigen. The HLA restriction and epitope specificity of the T cells can be determined by the specificity of multimeric complex binding to the T cells.

In a related aspect, binding of the T cells to the multimeric complexes provides a method for isolating antigen-specific T cells (e.g., by single-cell sorting using FACS). Thus, large numbers of T cells with known antigen specificities and MHC restrictions can be obtained, and optionally cultured to increase the number of T cells.

Multimeric MHC Class II Molecules

In one aspect of the invention, multimeric MHC class II/peptide complexes are provided that comprise human MHC class II molecules and peptides. The human MHC class II molecules are loaded with peptides to form MHC class II/peptide pairs. Suitable MHC class II molecules include heterodimers of MHC class II α and β subunits. Suitable α and β subunits include, for example, HLA-DPα, HLA-DPβ, HLA-DQα, HLA-DQβ, HLA-DRα and HLA-DRβ subunits. In specific embodiments, the MHC class II molecules can be, for example, DR1, DR2, DR4, DQ8, and the like. (See generally March, *Tissue Antigens* 51:467 (1998).)

The MHC class II molecules are typically soluble α and β polypeptides, such as the extracellular domains of the MHC class II α and β subunits. Soluble forms of the MHC class II α and β subunits typically include the α1 and α2 domains for the α subunits, and the β1 and β2 domains for the β subunit, respectively. In certain embodiments, the soluble forms of the MHC class II α and β subunits are the extracellular domains. Soluble α and β polypeptides can be derived from the native molecules, for example, by deletion of the cytoplasmic domain and/or deletion of the transmembrane domain. Soluble MHC class II molecules can be formed by, for example, proteolytic cleavage (e.g., papain), or by genetic manipulation and expression of a genetically engineered truncated forms of the molecules.

In other embodiments, the soluble forms of the α and β subunits typically do not include more than 15 residues of the transmembrane domain, typically less than 10 or 5 residues of the transmembrane domain. In yet other embodiments, soluble forms of the α and/or β subunits can include the extracellular domains and at least a portion of the cytoplasmic domains. The soluble forms of the α and β subunits typically retain the ability of the α2 or β2 domains, respectively, to fold into disulfide bonded structures.

In certain embodiments, the soluble forms of the α and β subunits are fusion proteins, to which additional domains can be added. Suitable domains include, for example, one or more leucine zippers, B cell (e.g., antibody) epitopes, labels, ligands for binding to a binding partner, modification sites, linker domains (e.g., a 15 to 25 amino acid peptide linker), secretion signals, and the like. For example, a leucine zipper domain can be linked to the carboxy termini of the soluble α and β subunits to facilitate association of those α and β subunits. Similarly, one or more linker regions can be included, such as between the soluble (extracellular) domain of an MHC class II α and/or β subunits and a leucine zipper domain. The linker region typically contains polar or amphipathic amino acids to allow a flexible, unconstrained solution conformation (also referred to as a conformationally flexible linker region), in which the geometry of the MHC class II molecule, or it subunits, is unrestricted relative to other domains. Such a linker is typically about 15 to about 25 amino acids, or more, in length. A modification site, such as a BirA modification site, can also be included in or linked to the soluble α and/or β subunit(s). In addition, one or more amino acids within the α and/or β subunits and/or within the linker regions or the leucine zipper domains, can be substituted.

The soluble α and β subunits are typically expressed in vivo in host cells and allowed to associate to form MHC class II molecules. Alternatively, the MHC class II molecules can be formed as a single chain fusion protein of the α and β subunits. For example, a single chain MHC class II molecule can be formed by linking nucleic acids encoding the soluble α and β subunits in a recombinant expression cassette. Such a fusion protein can optionally include a peptide linker domain (e.g., a 15 to 25, or more, amino acid peptide linker) between the α and β subunits.

In an exemplary embodiment, the MHC class subunits are formed by co-expressing nucleic acids cassettes encoding the α and β subunits in host cells. One expression cassette encodes a soluble MHC class II β subunit linked to a leucine zipper domain. A second expression cassette encodes a soluble MHC class II α subunit linked to a second leucine zipper domain. One of the expression cassettes typically includes a nucleic acid encoding a ligand binding domain and/or modification site. For expression, the cassettes can be inserted downstream (relative to the direction of transcription) of, and operably associated with, a promoter. The expression cassettes can be expressed from the same or different promoters.

For expression, the promoter can be selected according to the host cell. Suitable host cells include prokaryotic or eukaryotic cells, such as, for example, bacterial cells (e.g., *E. coli*, *B. subtilis*, and the like); insect cells (e.g., *Drosophila* Schneider S-2 cells); mammalian cells (e.g., CHO cells, COS cells, monkey kidney cells, lymphoid cells, and the like); fungal cells (e.g., *Saccharomyces cerevisiae*); and the like. Suitable promoters include, for example, the β-lactamase promoter (see, e.g., Villa-Komaroff et al., *Proc. Natl. Acad. Sci. USA* 75:3727–31 (1978)), the tac promoter (see, e.g., deBoer et al., *Proc. Natl. Acad. Sci. USA* 80:21–25 (1983)), or the T7 promoter for expression in *Escherichia coli*; the metallothionen promoter for expression in insect cells (see, e.g., Bunch et al., *Nucleic Acids Res.* 16:1043 (1988)); the SV40 early promoter region (see, e.g., Benoist and Chambon, *Nature* 290:304–10 (1981)), the promoter contained in the 3' long terminal repeat of Rous sarcoma virus (see, e.g., Yamamoto et al., *Cell* 22:787–97 (1980)), or the herpes thymidine kinase promoter (Wagner et al., *Proc. Natl. Acad. Sci. USA* 78:1441–45 (1981)), the regulatory sequences of the metallothionein gene (see, e.g., Brinster et al., *Nature* 296:39–42 (1982)) for expression in mammalian cells; the cauliflower mosaic virus 35S RNA promoter (see, e.g., Gardner et al., *Nucl. Acids Res.* 9:2871–88 (1981)), and the promoter of the photosynthetic enzyme ribulose biphosphate carboxylase (see, e.g., Herrera-Estrella et al., *Nature* 310:115–20 (1984)) for expression in plants; the Gal7 and Gal4 promoters, the alcohol dehydrogenase (ADH) promoter, and the phosphoglycerol kinase (PGK) promoter for expression in yeast; and the like.

In one exemplary embodiment, the expression cassette includes a promoter (e.g., a transcription initiation region) operably associated with, and in a 5' to 3' direction relative to the direction of transcription, a nucleic acid encoding a soluble MHC class II subunit and a leucine zipper domain (or single chain MHC class II fusion protein), and a transcriptional termination region, optionally having a polyadenylation (poly A) sequence. The expression cassette can include one or more restriction endonuclease sites and/or primer binding sites, as desired. Restriction endonuclease sites can be engineered by various means, such as, for example, site directed mutagenesis, polymerase chain reaction, and the like. (See generally Sambrook et al., *Molecular Cloning, A Laboratory Manual*, 3rd ed., Cold Spring Harbor Publish., Cold Spring Harbor, N.Y. (2001); Ausubel et al., *Current Protocols in Molecular Biology*, 4th ed., John Wiley and Sons, New York (1999); which are incorporated by reference herein.)

In another exemplary embodiment, the expression cassette includes a promoter (e.g., a transcription initiation region) operably associated with, and in a 5' to 3' direction relative to the direction of transcription, a nucleic acid encoding a soluble MHC class II subunit, a linker domain of about 10 to about 25 amino acids, and a leucine zipper domain, and a transcriptional termination region, optionally having a polyadenylation (poly A) sequence. The expression cassette can include one or more restriction endonuclease sites and/or primer binding sites, as desired.

The expression cassette can be part of an expression vector. Such an expression vector typically includes the expression cassette, one or more origins of replication, and one or more selectable markers (e.g., an antibiotic resistance gene). Suitable origins of replication include, for example, the pUC origin of replication in *E. coli*, an ARS1 or CEN sequence for replication in *S. cerevisiae*, and/or an SV40 origin for replication in mammalian cells. Suitable selectable markers include, for example, the ampicillin, tetracycline or neomycin resistance genes of *E. coli*; the LEU2, TRP1 or HIS3 genes for *S. cerevisiae*; the neomycin resistance gene for expression in mammalian cells; and the like. In other embodiments, the expression vector is an integrative vector without an origin of replication.

The MHC class II subunits can also be expressed in separate host cells and the MHC class II molecules formed in vitro. Conditions that permit formation of the MHC class II subunits in vitro are known in the art (see, e.g., Arimilli et al., *J Biol. Chem.* 270:971–77 (1995); Altman et al., *Proc. Natl. Acad. Sci. USA* 90:10330–34 (1993); Garboczi et al., *Proc. Natl. Acad. Sci. USA* 89:3429–33 (1992); the disclosures of which are incorporated by reference herein). In one exemplary embodiment, approximately equimolar amounts of MHC class II α and β subunits (e.g., MHC class II α and β subunit fusion proteins) can be mixed in the presence of a denaturing agent, such as urea. The subunits can be folded by dialysis of the denaturing agent from the mixture.

The MHC class II molecules, or subunits thereof, can be purified by methods known to the skilled artisan. Such methods include for example, affinity purification (e.g., antibody, an epitope tag, and the like); column chromatography (e.g., HPLC, FPLC, and the like), and other methods. For example, to purify DQ, DR and DP MHC class II molecules, SPVL-3, L-243 and B7/27 columns, respectively, can be used. (See, e.g., Ettinger et al., *J. Immunol.* 165:3232–38 (2000).) In an exemplary embodiment, HLA-DR molecules are purified by affinity chromatography using monoclonal antibody L243. (See, e.g., Stern and Wiley, *Cell* 68:465–77 (1992); Qu and Green, *DNA Cell Biol.* 14:741–51 (1995).) For general guidance in suitable protein purification methods, see Scopes, *Protein Purification*, Springer-Verlag, New York (1982).

Peptides

In another aspect, the MHC class II molecules are loaded with peptides. The peptides are typically loaded into the binding groove formed by the α1 and β1 domains and bind to the MHC class II molecules through non-covalent interactions. The peptides can be from about 9–10 to about 20 amino acids, or more, in length.

The peptides can be derived from any suitable antigen, such as a predetermined antigen. In certain embodiments, the predetermined polypeptide antigen is at least about 4 kilodaltons (kD), at least about 6 kD, or at least about 10 kD. Suitable predetermined antigens can include, for example, antigens of infectious agents, autoimmune antigens, tumor associated or tumor specific antigens, and the like. In exemplary embodiments, the predetermined antigen can be herpes simplex-2 virus VP16, tetanus toxoid, influenza hemagglutinin, human GAD65, prostate tumor antigen (PSA), HIV gag, allergen Lolp-1, melanoma tumor antigen tyrosinase, Cytomegalovirus PP65, insulin, IA-2, collagen, gp39, desmoglien, or any other suitable antigen. In other embodiments, the predetermined antigen can be an antigen of unknown function (e.g., identified from a genomic database, an expression library, an expressed sequence tag library, and the like).

Generally, pools of overlapping peptides are provided. Each of the peptides can be, for example, from about 9 or 10 to about 20 residues, or more, in length. The peptides are fragments of the predetermined antigen and/or fragments of a region of interest of the predetermined antigen. The peptides typically overlap (i.e., share a region of amino acid sequence identity) of between about two and about fifteen, or more, amino acid residues; for example, peptide n can be residues 1–20 of the predetermined antigen and peptide n+1 can be residues 9–28 of the predetermined antigen, etc. The skilled artisan will appreciate, however, that the length of the peptides and the amount residue overlap between peptides can vary, depending on the length of the predetermined antigen and/or region of interest, the degree of resolution required, and the like.

For longer polypeptide antigens, the overlapping peptides are typically sorted into peptide pools. The criteria for sorting the peptides into pools can vary, as will be appreciated by the skilled artisan. For example, in one embodiment, pools are provided of about 2 or about 3 to about 8 overlapping peptides (e.g., spanning a contiguous region of the antigen). In other embodiments, the peptides are sorted into pools according to any other suitable criteria, such that the peptides in each pool are known or can be determined. For shorter polypeptide antigens (e.g., 6–12 kD polypeptides), each pool can comprise at least two, typically from about 2 to about 8 peptides.

In any of the embodiments, the peptides can be prepared in a variety of ways. For example, peptides can be synthesized using an automated peptide synthesizer. The peptides can also be manually synthesized. (See, e.g., Hunkapiller et al., *Nature* 310:105–11 (1984); Stewart and Young, *Solid Phase Peptide Synthesis*, 2nd Ed., Pierce Chemical Co., Rockford, Ill., (1984); Houben-Weyl, *Methoden der organischen Chemie*, Vol. 15/1 and 15/2; Bodanszky, *Principles of Peptide Synthesis*, Springer Verlag (1984); the disclosures of which are incorporated by reference herein.) Alternatively, peptides can be synthesized by proteolytic cleavage (e.g., by trypsin, chymotrypsin, papain, V8 protease, and the like) or specific chemical cleavage (e.g., by cyanogen bromide). The peptides also can be synthesized by expression of overlapping nucleic acid sequences in vivo or in vitro, each nucleic acid sequence encoding a particular peptide.

The peptides optionally can be isolated and purified prior to contacting with the MHC class II molecules. Suitable methods include, for example, chromatography (e.g., ion exchange chromatography, affinity chromatography, sizing column chromatography, high pressure liquid chromatography, and the like), centrifugation, differential solubility, or by any other suitable technique for the purification of peptides or proteins. In certain embodiments, the peptides can be labeled (e.g., with a radioactive label, a luminescent label, a chemi-luminescent label, an affinity tag, and the like) to facilitate purification of the peptides (infra).

The peptides are typically not cross-linked to the MHC class II molecules. In other embodiments, the peptides optionally can be cross-linked to the binding groove of the MHC class II molecules. For example, bi-functional crosslinking reagents (e.g., hetero-bifunctional, homo-bifunctional, etc.) can be used to covalently link the peptides to the MHC class II molecules. (See Kunkel et al., *Mol. Cell. Biochem.* 34:3 (1981), which is incorporated herein by reference.) Suitable crosslinking reagents include, for example, dimethylsuberimidate, glutaraldehyde, succinimidyloxycarbonyl-α-methyl-α(2-pyridyldithio)-toluene (SMTP), N-succinimidyl 3-(2-pyridyldithio)-propionate (SPDP), sulfosuccinimidyl 4-(N-maleimidomethyl)cyclohexane-1-carboxylate (sulfo-SMCC), m-maleimidobenzoyl-N-hydroxysuccinimide ester (MBS), m-maleimidobenzoyl-N-hydroxysulfosuccinimide ester (sulfo-MBS), N-succinimidyl(4-iodoacetyl)aminobenzoate (SIAB), N-sulfosuccinimidyl(4-iodoacetyl)aminobenzoate (sulfo-SIAB), succinimidyl-4-(p-maleimidophenyl)butyrate (SMPB), sulfosuccinimidyl-4-(p-maleimidophenyl)butyrate (sulfo-SMPB), 1-ethyl-3-(3-dimethylaminopropylcarbodiimide hydrochloride (EDC), dithiobissuccinimidylpropionate (DSP), 3,3'dithiobis(sulfosuccinimidylpropionate) (DTSSP), and the like. (See, e.g., Pierce ImmunoTechnology Catalog and Handbook, Pierce Chemical Co. (1990), which is incorporated by reference herein.) In one embodiment, one or more anchor residues of a peptide can be cross-linked to the MHC class II molecule. In other embodiments, any suitable residue(s) of a peptide can be cross-linked to the MHC class II molecule.

Alternatively, the peptides can be prepared as fusion proteins with a soluble MHC class II β subunit. For example, nucleic acids encoding a peptide, or a mixture of peptides, can be expressed as a fusion protein comprising a peptide, a spacer or linker region (e.g., a 10–20 amino acid linker), a soluble MHC class II subunit, and a ligand binding domain. The peptide can be linked, for example, to the amino terminal end of the MHC class II β subunit. In one embodiment, the fusion protein is expressed from an expression cassette. The expression cassette can include, for example, a promoter operably associated with, and in a 5' to 3' direction relative to the direction of transcription, a nucleic acid encoding a polylinker cloning region, a nucleic acid encoding a spacer region, and a nucleic acid encoding an MHC class II β subunit. The expression cassette can be expressed in any suitable host organism and can be part of an expression vector. In another embodiment, pools of MHC class II/peptide fusion protein pairs can be prepared by inserting degenerate, semi-degenerate or non-degenerate nucleic acids into the polylinker region of an expression cassette, such as those described above. Alternatively, nucleic acids encoding a single peptide can be inserted into the polylinker region.

Identification of Candidate Epitopes

In another aspect, methods are provided for identifying candidate MHC class II epitopes. In certain embodiments, candidate epitopes can be identified using a computer-implemented algorithm for candidate epitope identification. Such computer programs include, for example, the TEPITOPE program (see, e.g., Hammer et al., *Adv. Immunol* 66:67–100 (1997); Sturniolo et al., *Nat. Biotechnol.* 17:555–61 (1999); Manici et al., *J Exp. Med.* 189:871–76 (1999); de Lalla et al., *J. Immunol.* 163:1725–29 (1999); Cochlovius et al., *J. Immunol.* 165:4731–41 (2000); the disclosures of which are incorporated by reference herein), as well as other computer implemented algorithms (infra).

The computer-implemented algorithm for candidate epitope identification can identify candidate epitopes in, for example, a single protein, in a very large protein, in a group of related proteins (e.g., homologs, orthologs, or polymorphic variants), in a mixtures of unrelated proteins, in proteins of a tissue or organ, or in a proteome of an organism. Using this approach, it can be possible to interrogate complex tissues or organisms based on sequence information for expressed proteins (e.g., from deduced open reading frame or a cDNA library), in addition to analysis of known candidate molecular targets, as an efficient, sensitive and specific approach to identification of T cell epitopes.

Following identification of candidate epitopes, peptides or pools of peptides can be formed that correspond to the candidate epitope(s). For example, once a candidate epitope is identified, overlapping peptides can be prepared that span the candidate epitope, or portions thereof, to confirm binding of the epitope by the MHC class II molecule, and, as necessary, to refine the identification of that epitope. Alternatively, pools of peptides can be prepared including a plurality of candidate epitopes identified using a computer-implemented algorithm for candidate epitope identification.

In an exemplary embodiment, the TEPITOPE program can be used. This program is based on a quantitative matrix algorithm for predicting peptide binding to MHC molecules. The program utilizes data from peptide-binding studies in which it was found that polymorphisms in MHC binding pockets dictate specificity. For example, the topography of pocket 9 of HLA-DR molecules has been found to be dependent on the DRB1 polymorphic residues 9, 37, 57, 60 and 61. The topography of a specific pocket can be generally independent of neighboring pockets, so that the constraints of pocket 9 for binding amino acid residues can be similar for different MHC alleles as long as they have identical DRB1 9, 37, 57, 60 and 61 residues.

The TEPITOPE program can be used to define pocket profiles and to minimize the number of peptide binding assays required to predict peptide binding properties. In the TEPITOPE program, results from peptide binding assays for small numbers of HLA molecules can be used to generate pocket profiles for a large number of HLA molecules. The combinations of the different modular pocket profiles can then be used to predict the overall peptide binding properties of a particular HLA molecule. The combinations of the different modular pocket profiles can be used to predict the overall peptide binding properties of antigens that contain promiscuous epitopes. The stringency of predicting peptide binding to a particular FIC can be set at different threshold values. For example, a setting of a 1% threshold implies that the peptides selected are the top 1% best binders. Similarly, a 10% threshold implies that the peptides selected are the top 10% best binders.

The identification of candidate peptide binding motifs can also be facilitated using both quantitative matrices (see, e.g., Marshall et al., *J. Immunol.* 154:5927–33 (1995); Hammer et al., *Adv. Immunol.* 66:67–100 (1997); Sturniolo et al., *Nat. Biotechnol.* 17:555–61 (1999); Rammensee et al., *Immunogenet.* 50:213–19 (1999); Brusic et al., *Bioinformatics* 14:121–30 (1998); Rammensee et al., *Immunogenet.* 41:178–228 (199); Southwood et al., *J. Immunol.* 160: 3363–73 (1998); Brusic et al., *Nucleic Acids Res.* 26:368–71 (1998); Hammer et al., *J. Exp. Med.* 180:2353–58 (1994); the disclosures of which are incorporated by reference herein) and neural network approaches (see, e.g., Brusic et al., *Bioinformatics* 14:121–130 (1998); Honeyman et al., *Nat. Biotechnol.* 16:966–69 (1998); the disclosures of which are incorporated by reference herein).

In an exemplary embodiment, a computer-implemented algorithm can be used to identify candidate epitopes in a predetermined antigen by analyzing the amino acid sequence of a predetermined antigen with the computer-implemented algorithm for candidate epitope identification to identify candidate epitopes. Peptides, or pools of peptides, comprising the candidate epitopes, or portions thereof can be prepared and tested in accordance with the present invention.

In another exemplary embodiment, a computer-implemented algorithm can be used to identify candidate epitopes in a proteome of an organism or a portion of a proteome of an organism (e.g., from a tissue or organ or developmental stage). The computer-implemented algorithm can analyze the amino acid sequences for candidate epitopes. Typically, protein or amino acid sequences are provided from genomic and/or proteomic databases. For example, amino acid sequences can be determined from the open reading frames, or coding sequences from a genomic databases. Amino acid sequences can also be derived from cDNA and/or EST libraries or databases; such a libraries or databases can represent the proteome of an whole organism or a portion of the organism (e.g., from a tissue, organ or developmental state). Protein or amino acid sequences can be determined from open reading frames using standard methodologies (e.g., using the GCG Wisconsin Package (Accelrys).)

Candidate epitopes can be identified using the a computer-implemented algorithm for candidate epitope identification. Peptides, or pools of peptides, comprising the candidate epitopes, or portions thereof, can be prepared and tested in accordance with the present invention.

In a related embodiment, methods are provided for identifying MHC class II epitopes by high throughput screening. Typically, protein or amino acid sequences are provided from genomic and/or proteomic databases. For genomic databases, the open reading frames, or coding sequences, can be used to determine the corresponding protein or amino acid sequences. Amino acid sequences can also be derived from cDNA and/or EST libraries or databases. Protein or amino acid sequences can be determined from open reading frames using standard methodologies. (Supra.) Candidate epitopes can be identified using the computer-implemented algorithm for candidate epitope identification. (Supra.) The computer-implemented algorithm for candidate epitope identification can identify epitopes in the entire genome or proteome, in a subset of the genome or proteome, in proteins or amino acid sequences from one or more tissues or organs, and the like.

Following identification of candidate epitopes, peptides or pools of peptides can be formed that correspond to the candidate epitope(s). For example, peptides can be prepared using an automated peptide synthesizer and sorted into pools. Overlapping peptides can be prepared that span the candidate epitope, or portions thereof, to confirm binding of the epitope by the MHC class II molecule, and, as necessary, to refine the identification of that epitope.

In a specific embodiment, the pools of peptides can be loaded into soluble MHC class II molecules to form multimeric MHC class II molecule/peptide complexes using an automated process (e.g., a robotic system). The complexes can then loaded into suitable assay format (e.g., 96 well or 384 well formats). Alternatively, the pools of peptides can be loaded to multimeric MHC class II molecules predispensed in the assay format.

The multimeric MHC class II molecule/peptide complexes can then be contacted with T cells under suitable binding conditions (e.g., such as by an automated or robotic process). The complexes are typically labeled so that binding of the complexes to the T cells can be detected. Following a suitable period of contacting, binding of the complexes to the T cells can be detected, such as, for example, by automated flow cytometry (e.g., a FACSCalibur) or other suitable assay method. Additional rounds of screening can be performed, as needed, to identify or refine the identification of MHC class II epitopes in the genome or proteome, or a subset thereof.

Formation of Multimeric MHC Class II/Peptide Complexes

In another aspect, the MHC class II molecules and peptides can be formed into multimeric MHC class II complexes. As used herein, forming multimeric MHC class II/peptide complexes can include forming multimeric MHC class II/peptide complexes from MHC class II molecule/peptide pairs and/or forming multimeric MHC class II molecules from MHC class II molecules, which can be loaded with peptides.

In various embodiments, the multimeric complexes can comprise two, three, four, or more MHC class II/peptide complexes. Such complexes can be formed by interaction between a ligand on the MHC class II molecules and a polyvalent binding partner. As used herein, the phrase "ligand-ligand binding partner pair" refers to a ligand and its ligand binding partner that are capable of recognizing and binding to each other. The term "polyvalent" refers to a ligand binding partner that has at least two binding sites, typically three or four, ligand binding sites. The ligand(s) and binding partner can be any moieties that are capable of recognizing and binding to each other to form a multimeric complex. Additionally, the ligand and binding partner can interact via the binding of a third intermediary substance. Typically, the ligand and ligand binding partner constituting the ligand-binding partner pair are binding molecules that undergo a specific noncovalent interaction with each other. The ligand and ligand binding partner can be naturally occurring or artificially produced, and optionally can be aggregated with other species of molecules.

Examples of ligands and ligand binding partners include, but are not limited to, biotin, avidin, streptavidin, agonists and antagonists for cell membrane receptors, receptors, toxins and venoms, viral epitopes, hormones such as steroids, hormone receptors, peptides, enzymes and other catalytic polypeptides, enzyme substrates, cofactors, drugs including small organic molecules, opiates, opiate receptors, lectins, sugars, saccharides including polysaccharides, proteins, and antibodies including monoclonal antibodies and synthetic antibody fragments. Examples of ligand-ligand binding partner complexes include the following: biotin-streptavidin; antibody-antigen; lectin-carbohydrate; peptide-cell membrane receptor; protein A-antibody; hapten-anti-hapten; digoxigenin-anti-digoxigenin; enzyme-cofactor; and enzyme-substrate. Optionally, ligand binding partners can be formed into polyvalent ligand binding partners according to other methods known in the art.

Typically, a ligand-ligand binding partner complex includes a binding partner that is polyvalent, i.e., capable of binding a plurality (e.g., 2, 3, 4 or more) ligands. In one embodiment, the ligand-binding partner complex is biotin-avidin or biotin-streptavidin, which can form a complex with one molecule of biotin and up to four molecules of streptavidin. The ligand can be part of the MHC class II molecule, or can be a modification attached to the MHC class II molecule, such as by a modifying enzyme. Suitable modifying enzymes include, for example, BirA, various glycosylases, farnesyl transferase protein, and the like. The MHC class II molecule, or a subunit thereof, can be modified by the modifying enzyme by introducing, for example, biotin, a sugar, a farnesyl group, and the like, for binding by the binding partner. The ligand can also be a B cell (e.g., antibody) epitope, either naturally-occurring or synthetic, such as for example, a polyoma epitope, a FLAG epitope, a hemagglutinin epitope for the 12CA5 monoclonal antibody, a polyhistidine tract, and the like. The binding partner can be an antibody, such as, for example, an IgG, IgM, and the like, or an antigen binding fragment thereof.

The binding partner can be free in solution or can be attached to a solid support. Examples of suitable solid supports include beads (e.g., magnetic beads), membranes, microtiter plates, and the like. The support can be glass, plastic (e.g., polystyrene), polysaccharide, nylon, nitrocellulose, PVDF, and the like. The use of a binding partner linked to a solid support can be useful for immobilization and/or isolation of T cells (e.g., such as from a population of PBMC) that recognize the multimeric MHC Class II molecule and the bound peptide.

In an exemplary embodiment, one of the MHC class II subunits includes a modification site (e.g., a BirA recognition sequence); BirA catalyzes biotinylation of the protein substrate. The biotinylated MHC class II molecule is then bound to a polyvalent binding partner (e.g., streptavidin or avidin), to which biotin binds with extremely high affinity. The multimers can then be stored until needed.

The MHC class II molecules typically are loaded with peptide by incubation at 37° C. in a phosphate buffer at slightly acidic pH (e.g., 100 mM sodium phosphate, pH 6.0) in the presence of 0.2% n-octyl-D-glucopyranoside (OG). A protease inhibitor is optionally added to the mixture. Suitable peptide loading times range from about 48 to about 72 hours, although greater and lesser times are within the scope of the present invention. Suitable peptide:MHC class molecule molar ratios are in excess of 10:1, although greater and lesser ratios are within the scope of the present invention. Other buffers and pH's can be used, as will be appreciated by the skilled artisan.

In certain embodiments, the multimeric MHC class II/peptide complexes are labeled. As used herein, the terms "label" or "labeled" refer to a molecule or groups of molecules which can provide a detectable signal when the label is incorporated into, or attached to, a polypeptide, such as a MHC class II molecule or a polyvalent binding partner. For example, a polypeptide or a polyvalent binding partner can be labeled with a radioactive molecule, a luminescent molecule, a fluorescent molecule, a chemi-luminescent molecule, an enzyme, or by biotinyl moieties. Methods of labeling polypeptides and binding partners are well known in the art. (See, e.g., Ausubel et al., supra; Sambrook et al., supra.) Examples of detectable labels include, but are not limited to, the following: radioisotopes (e.g., $^{3}H$, $^{14}C$, $^{32}P$, $^{35}S$, $^{125}I$, $^{131}I$, and the like), fluorescent molecules (e.g., fluorescein isothiocyanate (FITC), rhodamine, phycoerythrin (PE), phycocyanin, allophycocyanin, ortho-phthaldehyde, fluorescamine, peridinin-chlorophyll a (PerCP), Cy3 (indocarbocyanine), Cy5 (indodicarbocyanine), lanthanide phosphors, and the like), enzymes (e.g., horseradish peroxidase, β-galactosidase, luciferase, alkaline phosphatase), biotinyl groups, and the like. In some embodiments, detectable labels are attached by spacer arms of various lengths to reduce potential steric hindrance.

In specific embodiments, the binding partner can be labeled. For example, a biotinylated MHC class II molecule can be detected with labeled avidin or streptavidin (e.g., streptavidin containing a fluorescent molecule or a colored molecule produced by enzymatic activity that can be detected by optical or colorimetric methods). Alternatively, the MHC class II molecule can be detected, for example, with a labeled antibody or other binding agent that will bind specifically to the multimeric MHC class II complex. Suitable labels include any of those described above or known to the skilled artisan.

Contacting of T Cells with Multimeric MHC Class II Complexes

In another aspect, the multimeric MHC class II/peptide complexes are contacted with T cells to determine whether the complexes bind the T cells in an epitope-specific manner. In certain embodiments, the multimeric MHC class II/peptide complexes can be used to stain or detectably label the T cells. As used herein, "stain" refers to the ability of the multimeric MHC class II/peptide complexes to detectably label T cells that can bind the complexes in an epitope-specific manner.

Human T cells can be isolated from fresh samples from a human subject, from an in vitro culture of cells from a human subject, from a frozen sample of cells, and the like. Suitable samples can include, for example, blood, lymph, lymph nodes, spleen, liver, kidney, pancreas, tonsil, thymus, joints, synovia, and other tissues from which T cells can be isolated. Typically, the T cells are isolated as peripheral blood mononuclear cells (PBMC). PBMC can be partially purified, for example, by centrifugation (e.g., from a buffy coat), by density gradient centrifugation (e.g., through a Ficoll-Hypaque), by panning, affinity separation, cell sorting (e.g., using antibodies specific for one or more cell surface markers), and other techniques that provide enrichment of PBMC and/or T cells.

In one exemplary embodiment, PBMC are isolated from a blood sample by standard Ficoll-Hypaque method. The blood sample is treated with heparin and underlain with a Ficoll solution. Following centrifugation, the recovered cells can be washed, for example, in PBS or T cell culture medium (e.g., RPMI 1640 supplemented with 2 mM L-glutamine, 100 µg/ml penicillin/streptomycin, 1 mM sodium pyruvate and 15% pooled human serum; AIM-V; and the like). The washed cells can be resuspended in T cell culture medium, and the like.

The multimeric class II/peptide complexes can be contacted with the T cells to identify one or more MHC class II epitopes of a predetermined antigen. The epitopes can be determined according to the specificity of the α and β subunits comprising the MHC class II molecules.

Generally, the multimeric class II/peptide complexes are contacted with a sample of T cells of interest. In some embodiments, the T cells are cultured for between about 1–10 days, or more, in T cell culture media in the presence of the predetermined antigen to stimulate proliferation of T cells that are specific for that antigen. The media optionally can be supplemented other components for the culture and/or viability of T cells (e.g., serum, antibiotics, cytokines, co-stimulatory receptor agonists, and the like). In other embodiments, the T cells are contacted with the multimeric class II/peptide complexes without antigen stimulation and/or culturing (e.g., for patient monitoring).

The T cells are contacted with the multimeric MHC class 11/peptide pools under suitable binding conditions. In one embodiment, the binding conditions are 37° C. in any suitable T cell culture media (e.g., RPMI 1640 or AIM-V), phosphate buffered saline, Dulbecco's phosphate buffered saline, Dulbecco's Modified Eagle Medium, Iscove's medium, and the like. The media can be supplemented with other components for the culture and/or viability of T cells (e.g., serum, antibiotics, cytokines, and the like). The multimeric complexes are typically contacted with the T cells for at least about 5 minutes and typically within the range of about 1–2 hours. The appropriate concentration of multimeric complexes can be determined by titration.

The amount of multimeric complex bound to the T cells is determined. For example, if the T cells are substantially homogenous, then the amount of labeled multimeric complex can be directly determined, or determined using a labeled detection reagent, such as a labeled antibody, fluorescently labeled molecule, and the like. The cells are typically washed prior to detecting to remove unbound multimeric complex. Alternatively, the cells (e.g., PBMC) can be labeled with a secondary detection reagent (e.g., labeled anti-CD4 antibody), and the labeled T cells detected using a cell sorter or similar detection apparatus. By comparing the labeling of the T cells with different multimeric MHC class II/peptide complex pools, one or more peptide pools can be identified that contain an MHC class II epitope of the predetermined antigen.

The binding of the multimeric class II/peptide complexes to the T cells can also be detected by activation of the T cells. Generally, the multimeric class II/peptide complexes are contacted with a sample of T cells of interest. In some embodiments, the T cells are cultured for between about 1–10 days, or more, in T cell culture media in the presence of the predetermined antigen to stimulate proliferation of T cells that are specific for that antigen. The media can be supplemented with other components for the culture and/or viability of T cells (e.g., serum, antibiotics, cytokines, and the like). T cell activation can be determined using any of multiple standard activation criteria (e.g., labeled thymidine incorporation, cytokine release, expression of cell-surface activation markers, etc.). (See, e.g., Novak et al., *J. Immunol.* 166:6665–70 (2001); Kwok et al., *J. Immunol.* 164: 4244–49 (2000); Fraser et al., *Immunology Today* 14:357 (1993); Novak et al., *International Immunology* 13:799 (2001); the disclosures of which are incorporated by reference herein.)

In other embodiments, the multimeric MHC class II/peptide complexes can be immobilized on a substrate. T cells bind to the multimeric MHC class II/peptide complexes, and are also immobilized on the substrate. The amount of multimeric complex bound to T cells can be directly determined by washing away unbound T cells and labeling the immobilized T cells (e.g., with a labeled secondary antibody). By comparing the labeling of the T cells with different multimeric MHC class II/peptide complex pools, one or more peptide pools can be identified that contain an epitope of the predetermined antigen.

Alternatively, T cells bound to the multimeric MHC class II/peptide complexes immobilized on a substrate can be detected by determining T cell activation. Activation is measured using any of multiple standard criteria (e.g., labeled thymidine incorporation, cytokine release, expression of cell-surface activation markers, etc.).

In certain embodiments, one or more additional rounds (or cycles) of screening are performed, in which individual peptides in the identified peptide pool(s) are formed into multimeric MHC class II/molecule complexes and used to screen the sample of T cells. By analysis of the individual peptides, the epitope(s) can be localized to a peptide or peptides, or to a portion of one or more peptides. In related embodiments, additional peptides optionally can be synthesized to further define the epitope(s). For example, truncated peptides can be prepared to refine the identification of the epitope.

The specificity of the multimeric MHC class II/peptide complexes optionally can be confirmed by sorting labeled or stained T cells (i.e., that are positive for a particular peptide pool, or individual peptide), culturing those T cells, and then retesting (e.g., relabeling or staining) the cells with the multimeric MHC class II/peptide complexes. Alternatively, the specificity of the multimeric MHC class II/peptide complexes can be confirmed by T cell activation assay (e.g., labeled thymidine incorporation, cytokine release, expression of cell-surface activation markers, etc.), or by similar methods.

The stained or labeled T cells can optionally be collected, such as, for example, by using a fluorescence activated cell sorter (FACS), by collecting T cells from a substrate, and the like. The collected T cells can be cultured in vitro to increase (or expand) the number of T cells. In one embodiment, the collected T cells, with or without expansion, can be administered to a human subject.

In a related aspect, methods are provided for identifying an immunostimulatory epitope for a predetermined polypeptide antigen. The methods generally include preparing pools of overlapping peptides. Each peptide corresponds to a fragment of the predetermined polypeptide antigen. Each peptide typically shares a region of sequence identity with another peptide in the library. A library of pools of multimeric MHC class I/peptide complexes is formed by loading MHC Class II molecules with the peptide pools. In one embodiment, the soluble human MHC class II molecules are selected according to the MHC class II molecules of the human subject. Methods of determining the MHC class II molecules (e.g., the haplotype or genotype) of a human subject are well known to the skilled artisan.

The first library is contacted with T cells from a human subject. The T cells can be freshly isolated, from an in vitro culture, from an in vitro culture stimulated with antigen, from a frozen stock of cells, and the like. One or more pools of multimeric MHC class II/peptide complexes are identified that bind the T cells. The T cells can then, optionally, be screened with a second library of multimeric MHC class II/peptide complexes from the individual peptides of the at least one pool of multimeric MHC class II/peptide complexes of the first library that bind the T cells. By analysis of the first and/or second libraries, at least one epitope of the predetermined antigen is typically identified.

In a related aspect, methods for identifying a MHC class II epitope in a therapeutic polypeptide agent are provided. The therapeutic polypeptide agent can be any agent used to treat a disease or condition in a subject and broadly refers to a polypeptide agent, a polypeptide agent linked to a carrier or adjuvant, peptide, soluble peptide or other proteinaceous compound that is administered to a subject to reduce or alleviate one or more symptoms of a disease or condition.

The methods generally include preparing a library of peptide pools. Each peptide corresponds to a fragment of the therapeutic agent, such as, for example, a fragment of a polypeptide therapeutic agent. In one embodiment, the peptides share overlapping regions of amino acid sequence identity. A library of pools of multimeric MHC class II/peptide complexes is formed by loading MHC Class II molecules with the peptide pools. In a specific embodiment, the soluble human MHC class II molecules are selected according to the MHC class II molecules of the human subject to which the therapeutic agent will be administered. Methods of determining the MHC class II molecules of a human subject are well known to the skilled artisan, and include genotyping the subject or assaying the MHC class II molecules present on MHC class II containing cells.

The first library is contacted with T cells from the human subject. The T cells can be freshly isolated, from an in vitro culture, from an in vitro culture stimulated with the agent, from a frozen stock, and the like. One or more pools of multimeric MHC class II/peptide complexes can be identified that bind the T cells. The T cells can then optionally be screened with a second library of multimeric MHC class II/peptide complexes formed with the individual peptides of a pool of multimeric MHC class II/peptide complexes of the first library that bind the T cells. By analysis of the first and/or second libraries, at least one epitope on a therapeutic agent is typically identified. In some embodiments, the therapeutic agent can be designed or modified to exclude the MHC class II epitope on the therapeutic agent prior to administration to the subject.

Targeted Modulation of T Cells

In another aspect, methods are provided for targeted modulation of T cells using multimeric MHC class II/peptide complexes conjugated to biologically active modulatory molecules, such as antibodies or cytotoxins. The MHC class II/peptide complexes confer selective (e.g., epitope-specific) binding and targeting of the biologically active modulatory molecule to T cells. Generally, the methods include contacting a population of T cells with a multimeric MHC class II/peptide complex conjugated to a biologically active modulatory molecule. As used herein, the term "conjugated" refers to a covalent or non-covalent interaction between the multimeric MHC class II/peptide complexes and the biologically active modulatory molecule(s). The multimeric MHC class II/peptide complexes can be conjugated directly or indirectly to the biologically active modulatory molecule(s), as discussed in more detail below. One or more of the multimeric MHC class II/peptide complexes bind to an epitope-specific receptor on the T cell, whereby the biologically active modulatory molecule is brought adjacent to the T cell. The biologically active molecule can then bind to the cell, and modulate the state of the T cell. In some embodiments, the binding of the multimeric MHC class II/peptide complex to the T cell causes a first change in the state of the cell, and the binding of the biologically active modulatory molecule to the cell causes a second change in the state of the cell.

Suitable multimeric MHC class II/peptide complexes include any of those described supra and can be loaded with any suitable peptide. Typically, the peptide comprises an epitope from a predetermined antigen of interest. The population of T cells is known or suspected of having a T cell receptor for the MHC class II/peptide pair. Suitable predetermined antigens can include, for example, insulin, human GAD65, collagen, cartilage, gp39, myelin basic protein, proteolipid protein, IA-2, desmoglein, thyroglobulin, gliadin, and the like.

The multimeric MHC class II/peptide complexes can be conjugated, directly or indirectly, to biologically active modulatory molecules. As used herein, the term "biologically active modulatory molecule" refers to a molecule that can bind to T cell and induce or stimulate a change in the state in the cell. For example, the change in state can be the stimulation of apoptosis (e.g., the biologically active modulatory molecule is anti-CD95 antibody or CD95 Ligand (CD95L)), anergy, increasing proliferation of T cells (e.g., the biologically active modulatory molecule is IL-2 or a B7 molecule (e.g., B7.1 or B7.2)), T cell activation (e.g., upregulation of CD69 or CD4), deviation of T cells towards alternative cytokine production (e.g., the biologically active modulatory molecule is IL-12 or IL-4), and the like. Suitable biologically active modulatory molecules include, for example, apoptosis-inducing antibodies such as anti-CD95L antibodies, co-stimulatory antibodies to CTLA4 or CD28, cytotoxins, and the like. In a related embodiment, binding of the multimeric MHC class II/peptide complex can induce a first change in the state of a cell (e.g., T cell activation and upregulation of or CD95 or CD95L), and binding of the biologically active modulatory molecule can induce a second change in the state of the cell (e.g., stimulation of apoptosis). Suitable cytotoxins include, for example, measles hemagglutinin, diphtheria toxin, ricin, S. exotoxin, abrin, amantin, trichosanthin, restrictocin, and other cytotoxins and immunotoxins that can kill or inactivate T cells. Further, biologically active modulatory molecules can include those that induce T cell anergy by, for example, blocking certain co-stimulatory molecules (e.g., blocking CD28 activation by linking the MHC class II/peptide complexes to an anti-CD28 inhibitory antibody or to a soluble form of CTLA-4 that will block B7 binding to CD28).

In some embodiments, the antibodies bind to an apoptosis-inducing cell surface ligand (e.g., CD95L); these antibodies are capable of delivering an apoptotic signal leading to programmed cell death. Specific CD95 antibodies are also available that can deliver the apoptosis signal to the cell in the absence of CD95L cross-linking, a feature that can be desired considering the higher affinity interaction between antibody and ligand and relatively lower affinity between MHC class II/peptide pairs and the T cell receptor.

The soluble MHC class II molecules (or MHC class II/peptide pairs) can be coupled directly to the biologically active modulatory molecule, such as, for example, by a ligand-binding partner interaction, as described above. For example, biotinylated MHC class II/peptide pairs, or multimeric MHC class II/peptide complexes, can be conjugated to biologically active modulatory molecules treated with streptavidin or cross linking reagents. Alternatively, bi-specific antibodies can be used. For example, one specificity of the bi-specific antibody can be for MHC class II molecules and the other binding specificity can be for the biologically active modulatory activity.

In another embodiment, at least a plurality of multimeric MHC class II complexes (or MHC class II molecules) are conjugated to at least a plurality of biologically active modulatory molecules. For example, polymers of about 2 to about 10, at least about 20, at least about 50, or more subunits can be formed, each subunit having at least one multimeric MHC class II/peptide complex and at least one biologically active modulatory molecule.

Alternatively, the multimeric MHC class II/peptide complexes are coupled, directly or indirectly, to a substrate, such as a bead or microbead. For example, the MHC class II molecules labeled with biotin can be conjugated to commercially available multivalent streptavidin-coated beads. Alternatively, the multimeric MHC class II molecules are conjugated to a bead by anti-MHC class II antibodies which are coupled to the bead. The anti-MHC class II antibodies can be mono-specific or bi-specific, as described above.

Biologically active modulatory molecules can be antibodies including, but are not limited to, polyclonal antibodies, monoclonal antibodies, chimeric antibodies, single chain antibodies, antigen-binding antibody fragments (e.g., Fab, Fab', F(ab')$_2$, Fv, or hypervariable regions), and bi-specific antibodies. (See, e.g., Harlow and Lane, supra.) In some embodiments, polyclonal and/or monoclonal antibodies to an antigen are produced, whereby binding of the antibody to the antigen modulates the state of a T cell. In other embodiments, antibodies to a domain of an antigen are produced, whereby binding of the antibody to the antigen modulates the state of a cell.

Various procedures known in the art can be used for the production of polyclonal antibodies. For the production of such antibodies, various host animals (including, but not limited to, rabbits, mice, rats, sheep, goats, camels, and the like) can be immunized by injection with an antigen. Various adjuvants can be used to increase the immunological response, depending on the host species. Such adjuvants include, for example, Freund's adjuvant (complete and incomplete), mineral gels such as aluminum hydroxide, surface active substances such as lysolecithin, pluronic polyols, polyanions, peptides, oil emulsions, keyhole limpet hemocyanins, dinitrophenol, and other adjuvants, such as BCG (bacille Calmette-Guerin) and *Corynebacterium parvum*.

For preparation of monoclonal antibodies, any technique that provides for the production of antibody molecules by continuous cell lines in culture can be used. Such techniques include, for example, the hybridoma technique originally developed by Kohler and Milstein (see, e.g., *Nature* 256: 495–97 (1975)), the trioma technique (see, e.g., Hagiwara and Yuasa, *Hum. Antibodies Hybridomas* 4:15–19 (1993); Hering et al., *Biomed. Biochim. Acta* 47:211–16 (1988)), the human B-cell hybridoma technique (see, e.g., Kozbor et al., *Immunology Today* 4:72 (1983)), and the EBV-hybridoma technique to produce human monoclonal antibodies (see, e.g., Cole et al., In: *Monoclonal Antibodies and Cancer Therapy*, Alan R. Liss, Inc., pp. 77–96 (1985)). Human antibodies can be used and can be obtained, for example, by using human hybridomas (see, e.g., Cote et al., *Proc. Natl. Acad. Sci. USA* 80:2026–30 (1983)) or by transforming human B cells with EBV virus in vitro (see, e.g., Cole et al., supra).

Further to the invention, "chimeric" antibodies (see, e.g., Morrison et al., *Proc. Natl. Acad. Sci. USA* 81:6851–55 (1984); Neuberger et al., *Nature* 312:604–08 (1984); Takeda et al., *Nature* 314:452–54 (1985)) can be prepared. Such chimeric antibodies are typically prepared by splicing the genes (of one species) for an antibody molecule specific for an antigen together with genes from another species of antibody molecule of appropriate biological activity. It can be desirable to transfer the antigen binding regions (e.g., Fab', F(ab')$_2$, Fab, Fv, or hypervariable regions) of antibodies from one species into the framework of an antibody from another species by recombinant DNA techniques to produce a chimeric molecule. Methods for producing such "chimeric" molecules are generally well known and described in, for example, U.S. Pat. Nos. 4,816,567; 4,816,397; 5,693, 762; and 5,712,120; PCT Patent Publications WO 87/02671 and WO 90/00616; and European Patent Publication EP 239 400 (the disclosures of which are incorporated by reference herein). In a specific embodiment, the antibodies can be humanized. For example, a human monoclonal antibody or portions thereof can be identified by first screening a human B-cell cDNA library for nucleic acid molecules that encode antibodies that specifically bind to an antigen according to the method generally set forth by Huse et al. (*Science* 246:1275–81 (1989)). The nucleic acid molecule can then be cloned and amplified to obtain sequences that encode the antibody (or antigen-binding domain) of the desired specificity. Phage display technology offers another technique for selecting antibodies that bind to antigens. (See, e.g., International Patent Publications WO 91/17271 and WO 92/01047; Huse et al., supra.)

According to another aspect of the invention, techniques described for the production of single chain antibodies (see, e.g., U.S. Pat. Nos. 4,946,778 and 5,969,108) can be used. An additional aspect of the invention utilizes the techniques described for the construction of a Fab expression library (see, e.g., Huse et al., supra) to allow rapid and easy identification of monoclonal Fab fragments with the desired specificity.

Antibody fragments that contain the idiotype of the molecule can be generated by known techniques. For example, such fragments include but are not limited to, the F(ab')$_2$ fragment which can be produced by pepsin digestion of the antibody molecule, the Fab' fragments which can be generated by reducing the disulfide bridges of the F(ab')$_2$ fragment, the Fab fragments which can be generated by treating the antibody molecule with papain and a reducing agent, and Fv fragments. Recombinant Fv fragments can also be produced in eukaryotic cells using, for example, the methods described in U.S. Pat. No. 5,965,405 (the disclosure of which is incorporated by reference herein).

In another embodiment, bi-specific antibodies are provided. Bi-specific antibodies can be monoclonal antibodies that have binding specificities for at least two different antigens. For example, one of the binding specificities can be for an MHC class II molecule and the other one is for the biologically active modulatory antigen.

Methods for making bi-specific antibodies are known in the art. Traditionally, the recombinant production of bi-specific antibodies is based on the co-expression of two immunoglobulin heavy-chain/light-chain pairs, where the two heavy chains have different specificities (see, e.g., Milstein and Cuello, *Nature* 305:537–39 (1983), the disclosure of which is incorporated by reference herein). Because of the random assortment of immunoglobulin heavy and light chains, these hybridomas (quadromas) produce a potential mixture of different antibody molecules, some of which have the desired bi-specific structure. The purification of the correct molecule is usually accomplished by affinity chromatography steps. Similar procedures are disclosed in PCT Patent Publication WO 93/08829, and in Traunecker et al. (*EMBO J.* 10:3655–59 (1991)) (the disclosures of which are incorporated by reference herein).

Antibody variable domains with the desired binding specificities (antibody-antigen combining sites) can be fused to immunoglobulin constant domain sequences. The fusion typically is with an immunoglobulin heavy-chain constant domain, comprising at least part of the hinge, CH2, and CH3 regions. The first heavy-chain constant region (CH1) containing the site necessary for light-chain binding is usually present in at least one of the fusions. DNAs encoding the immunoglobulin heavy-chain fusions and, if desired, the immunoglobulin light chain, are inserted into separate expression vectors, and are co-transfected into a suitable host organism. For further details of generating bi-specific antibodies see, for example, Suresh et al. (*Methods in Enzymology* 121:210 (1986), the disclosure of which is incorporated by reference herein).

In the production of antibodies, screening for the desired antibody can be accomplished by techniques known in the art (e.g., ELISA (enzyme-linked immunosorbent assay)). (See, e.g., Harlow and Lane, *Using Antibodies, A Laboratory Manual*, Cold Spring Harbor Laboratory, New York (1999), the disclosure of which is incorporated by reference herein.)

In an exemplary embodiment, multimeric MHC class II/peptide complexes containing biotin are conjugated to streptavidin-coated beads. Anti-CD95L antibody is also coupled to the beads. Because CD95L is absent on naive CD4 T cells, the soluble MHC class II/peptide/anti-CD95L antibody complex (MHC class II/peptide, and anti-CD95L Ab complex ) bind to epitope specific T cells capable of recognizing the MHC class II/peptide pair on the bead. Binding of the MHC class II/peptide pair by the T cell activates that T cell, with concurrent upregulation of CD95. Anti-CD95 antibodies located on the same bead then deliver the apoptosis-inducing signal to the T cell, stimulating apoptosis.

The multimeric MHC class II/peptide/biologically active modulatory molecule complexes can be used in vivo or ex vivo to target epitope-specific T cells. In some embodiments, T cells are isolated from a subject, contacted with the multimeric MHC class II/peptidelbiologically active modulatory molecule complexes for a time sufficient to modulate the state of at least one T cell in the T cell population, followed by administration of the T cells to the subject.

In another embodiment, the multimeric MHC class II/peptide/biologically active modulatory molecule complexes are administered intravenously to the subject, whereby the modulatory effect is induced in vivo. The dose for individual subjects and for different diseases or conditions can be determined, for example, by procedures known to those of skill in the art. In certain embodiments, doses of the complexes can be based on the doses of the peptide component, which can be administered, for example, at between about 5 to about 200 mg per dose. For each form of multimeric MHC class II/peptide/biologically active modulatory molecule complexes, the ratios of the peptide to multimeric MHC class II complex and to biologically active modulatory agent can be stoichiometric. Thus, the doses of the complexes can be determined from the peptide doses. The complexes can be administered, for example, one or more times per day, and administration can be performed, for example, for one to four weeks.

As the skilled artisan will appreciate, the MHC status of the subject can be monitored during the administration of the complexes and the dose of the complexes adjusted accordingly. For example, by measuring the effect of the complexes on certain parameters (e.g., the presence of autoimmune T cells, T cell activation, proliferation, cytokine secretion, and the like), the doses of the complexes can be increased or decreased, accordingly. In addition, the doses of the complexes can be repeated periodically, depending upon the particular disease.

The complexes can be administered in variety of modes of administration. In certain embodiments, the complexes can be administered parenterally, and formulated for example, as an injectable dosage form (e.g., a solution, suspension, emulsion, and the like). Such a formulation can optionally be formulated with a pharmaceutically acceptable parenteral vehicle. Such vehicles are preferably non-toxic, and can include, for example, water, saline, Ringer's solution, dextrose solution, and Hanks' solution. Non-aqueous vehicles, such as fixed oils and ethyl oleate, can also be used. The vehicle can optionally include minor amounts of additives, such as substances that enhance isotonicity and chemical stability, e.g., buffers and preservatives. The complexes can be formulated in purified form substantially free of aggregates and other proteins at concentrations of, for example, about 1 to about 50 mg/ml. Suitable pharmaceutical vehicles and their formulations are described in, for example, *Remington's Pharmaceutical Sciences*, by E. W. Martin, which is incorporated herein by reference.

The multimeric MHC class II/peptide/biologically active modulatory molecule complexes can be used to eliminate epitope-specific T cells from a population of lymphocytes. Such an elimination of epitope-specific cells from a population of T cells can be used to induce immune tolerance (deletional tolerance), to treat an autoimmune condition in a subject (e.g., a human or non-human vertebrate), and the like. Suitable autoimmune conditions include, for example, autoimmune diabetes, rheumatoid arthritis, multiple sclerosis, pemphigus vulgaris, celiac disease, autoimmune thyroid disease, and the like.

Determining and Monitoring MHC Class II Status

Methods of determining and monitoring an MHC class II-restricted immune status of a subject are also provided. Such methods generally include isolating T cells from the subject by any suitable method. The T cells can be, for example, isolated as PBMC. The T cells are contacted with multimeric MHC class II/peptide complexes comprising soluble MHC class II molecules and peptides comprising at least one MHC class II epitope of interest. The MHC class II-restricted immune status can include the presence or absence T cells that can bind to at least one (e.g., one or more) MHC class II epitopes. For example, the MHC class II epitope can be an autoantigen, a tumor-associated or tumor-specific antigen (e.g., prostate specific antigen), and the like. The T cells are then examined to determine whether the T cells bind the multimeric MHC class II/peptide complexes (e.g., by staining or detection of a label). Alternatively, the T cells can be examined to determine whether the T cells are activated by the multimeric MHC class II/peptide complexes (e.g., by proliferation assay or cytokine assay).

These methods allow the monitoring of the MHC class II epitope status of the subject. According to methods of the present invention, soluble multimeric MHC class II/peptide complexes can be used to identify epitope-specific T-cells in a subject. For example, such a subject can have, or can be at-risk for, an autoimmune disease or condition (e.g., autoimmune (Type 1) diabetes, rheumatoid arthritis, multiple sclerosis, pemphigus vulgaris, celiac disease, autoimmune thyroid disease, and the like). In a specific embodiment, T cells from a subject can be contacted with soluble multimeric MHC class II/peptide complexes using a peptide having an MHC class II epitope correlated with an autoimmune condition. Following contacting, the appearance of highly activated T-cells and the up-regulation of certain T cell markers (e.g., a CD25/CD4$^{high}$ phenotype) can indicate a diagnosis of, or predisposition to, autoimmune disease. Such a method is particularly advantageous where low precursor frequency and/or low level of labeling or staining of the total population of CD4+ T cells is evident.

In a specific embodiment, the activation of T cells and the upregulation of certain cell surface markers (e.g., CD4) can indicate the presence of activated T cells to an autoimmune antigen associated with Type 1 diabetes (e.g., GAD65). For example, T cell can be isolated from a subject and contacted with soluble multimeric MHC class II/peptide complexes comprising a GAD65 epitope. The activation of T cells and the up-regulation of T cell markers (e.g., CD25/CD4) can indicate a prognosis, diagnosis or predisposition to Type 1 diabetes. The epitope is typically selected to be correlated or associated with an autoimmune condition or disease. Typically, the epitope does not cause a T cell activation profile in normal subjects (i.e., healthy individuals who are not at-risk for developing the autoimmune condition.

The phenotyping of T-cells according to the present invention also provides useful markers for progression of immune-mediated B-cell reactivity and can be utilized in clinical trials to evaluate the efficacy of the immunomodulatory therapies targeting intervention/prevention of Type 1 diabetes. For example, a subject having an autoimmune disease (e.g., autoimmune diabetes, rheumatoid arthritis, multiple sclerosis, pemphigus vulgaris, celiac disease, autoimmune thyroid disease, and the like) can be treated with an immunosuppressive therapeutic agent or a therapeutic agent for selectively deleting T cells (as described supra). The number of T cells labeled or stained with multimeric MHC class II/peptide complexes containing the MHC class II epitope can be correlated with the efficacy or effectiveness of the agent. A decrease in the number of stained T cells can indicate that the agent is effective while an increase (or lack of decrease) can indicate that the agent is not effective in the patient.

Alternatively, the MHC class II epitope of the patient having a hyperproliferative disease (e.g., cancer, metastasis, tumor, or other abnormal cell growth, enlargement or replication) can be monitored. The number of T cells stained or labeled with multimeric MHC class II/peptide complexes containing the MHC class II epitope can be correlated with the efficacy or effectiveness of the agent. For example, if the patient is receiving an immunostimulatory agent, an increase in the number of stained T cells can indicate that the agent is effective while a decrease (or lack of increase) in the number of stained T cells can indicate that the agent is not effective in the patient.

In some embodiments, the T cells are screened without amplification to determine the number of T cells having the MHC class II epitope of interest. In other embodiments, T cells can be cultured in vitro, with or without stimulation with peptide or polypeptide comprising the epitope before contacting the T cells with the multimeric MHC class II/peptide complexes.

EXAMPLES

The following examples are provided merely as illustrative of various aspects of the invention and shall not be construed to limit the invention in any way.

Example 1

In this example, a panel of 60 overlapping HSV-2 VP16 peptides were analyzed to identify MHC class II epitopes in HSV-2 VP16.

Methods and Materials

Generation of DRA1*0101/DRB1*0401 and DRA1*0101/DRB1*0404 Tetramers

Soluble human MHC class II α and β chains were expressed using a *Drosphila* Schneider S-2 cell system. The MHC class II α and β chains were expressed from separate expression vectors, pRMHa-2 alpha and pRMHa-3 beta, which are derived from the Cu-inducible pRmHa-3 *Drosophila* expression vector. The alpha chain was expressed from an expression cassette that includes the metallothionen promoter upstream of soluble MHC class II α chain which is fused to a leucine zipper coding region. The beta chains was expressed from a similar expression cassette that includes the metallothionen promoter upstream of the MHC class II β chain, which is fused to a leucine zipper coding region and a biotinylation coding sequence. These expression cassettes containing the coding regions for MHC class II α and β chains were made using the PCR-mediated splicing overlap techniques. The assembly of the DRA1*0101 and DRB1*401 constructs was described by Novak et al. (*J. Clin. Invest.* 104:R63–67 (1999)) and Kwok et al. (*J. Immunology* 164:4244–49 (2000)) (the disclosures of which are incorporated by reference herein).

A similar approach was used to generate the DRB1*0404-leucine zipper-biotinylation site expression vector from DRB1*0404 cDNA. (DRB1*0404 cDNA was isolated from the EBV-transformed B-LCL Bin-40, and was a gift from Dr.

P. Gregersen, North Shore University Hospital, Manhasset, N.Y.) Briefly, a chimeric cassette containing the extracellular coding region for the DRB1*0404 chain appended to the acidic leucine zipper motif was generated from DRB1*0404 and leucine zipper cDNA using the PCR-mediated splicing overlap technique (see Horton et al., *Biotechniques* 8:528 (1990); Chang et al., *Proc. Natl. Acad. Sci. USA* 91:11408 (1994)). The same primers were used as described above for isolating the DRA1*0101 and DRB1*0401 clones. A site-specific biotinylation sequence was then added to the 3' end of the DRB1*0404/leucine zipper cassette. The chimeric cDNA was subcloned into the Cu-inducible pRmHa-3 Drosophila expression vector.

The pRMHa-2 alpha and pRMHa-3 beta expression vector were transfected into Drosophila Schneider S-2 cells by standard techniques. Single cell clones were isolated by limited dilution. The isolated clones were screened for expression of soluble MHC class II molecules by dot blot with anti-HLA antibodies. Clones were selected for further expansion and culture supernatants were used for soluble MHC class II molecule purification.

Soluble MHC class II molecules were isolated from the supernatant of the S-2 cells, following addition of $CuSO_4$, by affinity chromatography. Briefly, transfected S-2 cells were grown to a density of $5 \times 10^6$/ml, and $CuSO_4$ (1 mM) was used to induce MHC class II secretion. Supernatants were harvested 5 days after $CuSO_4$ induction. Affinity purification was performed as follows: To purify, DQ, DR and DP molecules, SPVL-3, L-243 and B7/27 antibody columns, respectively, were used. The culture supernatant (from the transfected S-2 cells induced with $CuSO_4$) with 0.05% octyl-glucopyranoside (OG) were loaded onto the affinity column at a flow rate of approximately 1 ml/minute. The column was washed with (i) 200 ml of 1×PBS, 0.05% OG; (ii) 50 ml of 1×PBS, 0.5M NaCl, 0.05% OG; and (iii) 50 ml 10 mM Tris, pH 7.5, 0.5M NaCl. The affinity purified-MHC class II molecules were eluted with a buffer of 0.1M Tris, 0.5M NaCl, pH 11.2. About 2 milliliters of sample was collected and pooled; acetic acid was added immediately added to neutralize the pH of the collected sample. The pH of the pooled sample was further adjusted to between pH 6 to pH 7.

The protein in the sample was concentrated to approximately 1 to 2 mg/ml, and then dialyzed against biotinylation buffer (10 mM Tris, pH 8 and 10 mM NaCl) and biotinylated using the BirA enzyme (Avidity, Denver, Colo.) (see Schatz, *Biotechnology* 11:1138 (1993), the disclosure of which is incorporated by reference herein) according to manufacturer's recommendations. The biotinylated protein was further dialyzed into 100 mM phosphate buffer pH 6.0. The biotinylated MHC class II molecules were then ready for loading with peptide. Detailed methods for MHC class II molecule purification can also be found in Kwok et al. (*J. Immunology* 164:4244–49 (2000)) and Ettinger et al. (*J. Immunology* 160:2365–73 (1998)).

For generation of tetramer pools, a panel of 60 overlapping HSV-2 VP16 peptides, p3 to p62, were used. These peptides, each 20 amino acids in length, corresponded to the entire VP16 protein with a 12 amino acid overlap between adjacent peptides. Peptides were synthesized on polyethylene pins using 9-fluorenylmethoxycarbonyl (FMOC) chemistry by Chiron Technologies (Clayton, Australia). Individual peptides were weighed out and dissolved in DMSO to achieve the appropriate peptide concentration. The peptides were divided into 12 pools, each containing 5 different overlapping peptides. Five peptides per pool was found to preserve sensitivity to allow identification of individual peptide epitopes.

Pools of the biotinylated class II molecules DR0401 and DR0404 were each loaded with the 12 different peptide pools by incubation for 48–72 hours at 37° C. with a 25-fold molar excess of peptides (total) in 100 mM sodium phosphate, pH 6.0 and 0.2% n-octyl-D-glucopyranoside. Briefly, equal volumes of octyl-glucopyranoside (5 mg/ml) and MHC class II molecules (1 mg/ml) were combined. Peptides were added to a final concentration of 1 mg/ml. A protease inhibitor, PEFABLOC® (4-(2-Aminoethyl)-benzenesulfonyl-flouride, hydrochloride; Boehringer Mannheim), was then added to a final concentration of 1 mg/ml, and the mixture was incubated for 48–72 hours at 37° C.

Tetramers were formed by incubating the MHC class II/peptide pairs with phycoerythrin (PE)-labeled streptavidin (Biosource International, Camarillo, Calif.). The fluorochrome-conjugated streptavidin (1:8 molar ratio of streptavidin to MHC class II molecule) was added, and the mixture incubated at room temperature for six hours to overnight in the dark to form multimeric MHC class II/peptide complexes. For single peptide tetramers, the peptide was loaded at a concentration of 5-fold molar excess over the MHC class II molecule concentration. The multimeric complexes could then be stored at 4° C. in the dark.

Staining and Isolation of VP-16 Specific T Cells:

Peripheral blood mononuclear cells (PBMC) were isolated from blood samples of a DRB1*0401, DRB1*0404 HSV-2 positive individual by standard Ficoll-Hypaque method. Briefly, 15–17 ml heparinized blood was diluted 1:1 with 1×PBS in a 50 ml vial. 10 ml Ficoll was underlain under the heparinized blood. The vials were spun for 20 min at 2000 rpm. The mononuclear cells at the interface were collected, and washed three times with 1×PBS. The cells were resuspended at a density of $10 \times 10^6$ cells/ml in T cell culture medium (RPMI 1640 supplemented with 2 mM L-glutamine, 100 µg/ml penicillin/streptomycin, 1 mM sodium pyruvate and 15% pooled human serum).

Peripheral blood mononuclear cells (PBMC) were stimulated with VP16 protein at 2 µg/ml (a gift from Chiron Corporation, Emeryville Calif.). IL-2 was added (10 U/ml final) every other day starting on day 5. T cells were stained with tetramer pools on day 11 or 12. Briefly, T cell growth medium was used throughout the staining process. PBMC were washed one time in T cell growth medium. For each pool, $2 \times 10^5$ cells were incubated with 0.5 µg PE-labeled tetramer in 50 µl of culture media (10 µg/ml) at 37° C. for 1 to 2 hrs, and then stained with anti-CD4-FITC (PharMingen, San Diego, Calif.) for 15 min at room temperature. Near maximal staining of T cell clones was observed with 0.05 µg tetramer reagent, indicating that 10 µg/ml provides an excess of MHC molecules for the staining reaction. Cells were washed two times and analyzed using a Becton Dickinson FACS Calibur flow cytometer (Becton Dickinson, San Jose, Calif.).

Tetramers loaded with the corresponding single peptides were generated for those pools which gave positive staining, and analysis was done on day 14 or 15. Levels of background staining, generally around 0.1%, were determined using tetramers loaded with an irrelevant peptide (influenza A hemagglutinin protein, residues 307–319, ($HA_{307-319}$)). Cells which were positive for a particular tetramer were single cell sorted into 96-well U-bottom plates using a FACS Vantage on the same or following day. Sorted cells were expanded with $1.5 \times 10^5$ unmatched, irradiated (5,000 rads) PBMC per well as feeders with 2.5 µg/ml PHA and 10 U/ml IL-2 added 24 hours later. The specificity of cloned T cells was confirmed by staining with tetramers (loaded with cognate peptide or control peptide, $HA_{307-319}$) and T cell proliferation assays using 10 μg/ml of specific peptide and BLS-DRA1*0101/DRB1*0401 (BLS-DR0401) or BLS-DRA1*0101/DRB1*0404 (BLS-DR0404) as antigen presenting cells (Novak et al., supra; Kovats et al., *J. Clin. Invest.* 96:217 (1995)). Competition binding assays of identified peptides were performed using purified DR0401 and DR0404 protein as previously described (Ettinger et al., *J. Immunol.* 160:2365 (1998)).

Measurement of Cytokine Secretion:

In experiments using IFNγ secretion as an indicator of T cell reactivity, PBMC were stimulated with HSV-2 VP16 protein as described above and assayed on day 11 or 12. $1 \times 10^5$ PBMC were incubated together with an equal number of BLS-DR0401 or BLS-DR0404 antigen presenting cells that had been pulsed with 50 μg/ml of each peptide pool. Following a 3 hour incubation, IFNγ secretion was determined by use of a cytokine secretion capture assay following the protocol supplied by the manufacturer (Miltenyi Biotec, Auburn, Calif.) (see Brosterhus et al., *Eur. J. Immunol.* 29:4053 (1999)). Briefly, cells were washed once in PBS and incubated in 100 μl media on ice for 5 minutes with an antibody-antibody conjugate directed against both CD45 and IFNγ. Pre-warmed media was added to a final volume of 2 milliliters, and cells were incubated at 37° C. for 45 minutes under gentle rotation to allow cell-surface capture of secreted IFNγ. Cells were washed once in PBS and then stained for 15 minutes on ice using a second PE-conjugated antibody directed against IFNγ as well as a FITC-conjugated antibody directed against CD4. Cells were washed once in PBS and analyzed by flow cytometry as described above. For pools which showed significant IFNγ staining, reactivities of individual peptides were assayed using the same approach.

Results

Epitope Mapping Using MHC Class II Tetramer Pools:

To determine the class II restricted epitopes of the HSV-2 VP16 protein, peptides of 20 amino acids in length, spanning the entire sequence of the VP16 protein, with 12 amino acid overlap between consecutive peptides, were used to generate two tetramer panels, one for the DR0401 molecules and the other for the DR0404 molecules. Each panel included 12 different tetramer pools, designated as pool 1 to pool 12. Each pool contained tetramers of soluble MHC class II molecules together with five different peptides of the VP16 protein.

Using these two tetramer panels, PBMC were analyzed from a DRB1*0401, DRB1*0404 HSV-2 positive individual. Cells were stimulated with 2 μg/ml of VP16 protein and 11 or 12 days following stimulation were stained with each tetramer panel. Four pools, 2, 5, 6 and 12, gave significant staining above background using the DR0401 tetramer panel. Staining with the DR0404 tetramer panel identified two pools, pools 6 and 12, as having significant staining. Based on these results, tetramers loaded with the individual peptides of the positive pools and used to determine which peptide epitopes in the pool were recognized by responding T cells. For DR0401/pool 2, peptides p9, p10 and p12 gave positive staining; for DR0401/pool 6, peptide p32 gave positive staining; and for DR0401/pool 12, peptides p61 and p62 gave positive staining. Individual stimulatory peptides could not be identified from pool 5 despite repeated attempts. This difficulty may reflect T cells of low avidity that are difficult to consistently stain using tetramers. For DR0404/pool 6, peptides p31 and p32 gave positive staining; and for DR0404/pool 12, peptide p58 showed positive staining.

To assess the efficiency of pooled-peptide tetramers in identifying T cell epitopes, the approach describe above was compared that of Kern and colleagues who utilized IFNγ production as an indicator for epitope specific cells (Kern et al., *Nat. Med.* 4:975 (1998)). Cells were stimulated with 2 μg/ml of VP16 protein and 11 or 12 days following stimulation were restimulated for 3 hours using BLS-DR0401 or BLS-DR0404 cell lines pulsed with 50 μM of each peptide pool. For PBMC stimulated with the BLS-DR0401 cell line, pools 2, 5 and 12 were positive for IFNγ secretion as measured by flow cytometry. Both pools 2 and 12 were positive in the DR0401 tetramer analysis. Pool 5 was positive in the tetramer screen; however, as noted above no tetramer staining was detected with individual peptides of pool 5. Interestingly, pool 6, which was positive in the tetramer screen, did not show appreciable IFNγ production. This suggests that while the two methods generally coincide, differences in what each approach measures—TCR/MHC avidity with tetramers and specific effector function with IFNγ production—allow each method to identify occasional cells which would be undetectable by the alternate approach.

Characterization of Tetramer Positive T Cell Clones:

T cells that were specific for peptides p10 and p61 for DR0401, and peptide p58 for DR0404, were isolated and tested for specificity. Tetramer positive T cells were single-cell sorted and expanded, and more than 20 clones specific for each DR/peptide complex were identified. All of the clones obtained demonstrated antigen specificity as shown by proliferation assays and tetramer staining. Though strong staining and antigen-specific proliferation were observed for most clones, there existed variations in staining intensity and degree of proliferation for a number of clones. For example, atypical staining patterns were observed with DR0401 restricted clones specific for p10. Both clones p10-1 and p10-2 consistently showed a broader range of staining intensity compared to the majority of clones, which showed more focal staining. Clone p10-3, on the other hand, consistently showed poor tetramer staining despite vigorous proliferation to specific peptide. These different staining patterns may reflect different avidities of the T cell receptor for the MHC class II/peptide complex in the different clones. These atypical staining patterns were not unique to clones restricted to p10; a few clones specific for p58 and p61 also showed weak staining while clones specific for p10 with strong staining were also observed.

In order to more precisely define the epitopes recognized by the T cell clones, probable DR0401 and DR0404 peptide binding motifs were evaluated using truncation analyses. A number of studies have extensively characterized the peptide binding motifs for DR4 (see, e.g., Sette et al., *J. Immunol.* 151:3163 (1993); Marshal et al., *J. Immunol.* 154:5927 (1995); Rammensee et al., *Immunogenet.* 41:178 (1995)). Examination of peptide p10 (VP16 57–76) revealed that the 12-mer peptide VP16 58–69 possesses good DR0401 binding motifs. Experiments using the VP16 58–69 peptide demonstrated that the peptide could indeed stimulate the DR0401 restricted T cell clones specific for the p10 epitope. These data suggest that the positive staining observed with the DR0401/p9 tetramers was likely due to the overlapping of peptide p9 (VP16 49–68) and peptide p10 (VP16 57–76) as both peptides contain the shorter epitope (PMPVP-PAALFN; SEQ ID NO: 1).

Similar examination of peptide p61 (VP16 465–484) identified a 13-mer peptide VP16 472–484 (TDVSLGDEL- RLDG; SEQ ID NO: 2) which stimulated DR0401 restricted T cell clones directed against the p61 epitope. Therefore, the positive staining seen with the DR0401/p62 tetramer was likely due to the overlapping of peptides p61 and p62. These results also demonstrate that tetramer staining using overlapping peptides provides an alternative approach to directly mapping minimal epitopes. Truncation studies with peptide p58 refined the DR0404 restricted epitope to the 12-mer VP16 443–454.

The DR0401 restricted and the DR0404 restricted epitopes as characterized in the truncation studies are listed in Table I. Interestingly, the DR0404 restricted 443–455 epitope is not found as a DR0401 restricted epitope, nor are the 58–69 and 472–484 DR0401 restricted epitopes found as DR0404 restricted epitopes. In vitro peptide binding was analyzed using purified DR0401 and DR0404 molecules. Peptides from the DR0401 restricted epitopes (VP16 58–69 and 472–484) bind with a much lower affinity to DR0404 compared to the DR0404 restricted peptide VP16 443–454 (Table I). On the other hand, the affinity of the DR0404 443–455 epitope for DR0401 is lower when compared to peptides 58–69 and 472–484, although the magnitude of this difference is not as great with peptide 58–69 (Table I). These experimental observations are in agreement with previous reports that the limited polymorphism between these alleles at codons 86 and 71 of the DRB1 chain may dictate unique binding patterns, although factors other than peptide binding are likely also important in dictating which epitopes become immunodominant for each allele (Demotz et al., *Eur. J. Immunol.* 23:425 (1993); Dessen et al., *Immunity* 7:473 (1997)).

TABLE I

Relative binding affinity of
DR0401 and DR0404 restricted VP16 epitopes*

| | $IC_{50}$ 0401 | $IC_{50}$ 0404 |
|---|---|---|
| DR0401 restricted VP16 epitopes: | | |
| VP16 58–69 AL<u>F</u>NRLLDDLGF (SEQ ID NO: 3) | 2 µM | 4 µM |
| VP16 472–484 DFE<u>F</u>EQMFTDAMG (SEQ ID NO: 4) | 0.5 µM | 0.5 µM |
| DR0404 restricted VP16 epitopes: | | |
| VP16 443–455 FD<u>L</u>EMLGDVESPS (SEQ ID NO: 5) | >5 µM | 0.005 µM |

*Underlined residue is the proposed first anchor for binding to the respective allele as determined by peptide truncation studies.

To determine whether relevant peptides in each pool will be outcompeted by irrelevant peptides present in the pool, DR0401 class II molecules were loaded with different molar ratios of cognate peptide (VP16 p61) to competitor peptide ($HA_{307-319}$). These mixed tetramers were used to stain a DR0401/p61 clone. In competition experiments, these two peptides possess similar affinities for the DR0401 molecule. There was no significant difference in staining pattern when the molar ratio of p61 to $HA_{307-319}$ was 1:1. An appreciable decrease in staining intensity of the DR0401/p61 clone was observed with a 1:10 molar ratio; nonetheless, staining of clones with these mixed tetramers was still 10-fold above background. Likewise, similar staining above background was observed using cognate tetramer diluted 100-fold, suggesting that an excess of class II molecules are present during the staining reaction. These findings suggest that loading of peptide mixtures onto MHC class II molecules within the parameters described will not preclude complex staining of antigen specific T cells of interest.

Example 2

In this example, a comparison is made of T cell epitopes as selected by the TEPITOPE program and those identified by the TGEM method.

Computer-Implemented Identification of Candidate Epitopes.

Human subjects infected with HSV-2 mount T cell responses to viral antigens, including CD4+ T cell responses to peptides from the VP16 tegument protein (see Koelle et al., *J. Virol.* 72:7476–83 (1998)). Using methods according to the present invention, peripheral blood T cells from HSV-2 infected individuals carrying HLA DRB1*0101, DRB1*0401, DRB1*0402, DRB1*0404, DRB1*1104 and DRB1*1501 MHC class II alleles were tested for their ability to bind specific MHC-VP16 epitope tetramers. VP16 T cell epitopes identified by methods of the present invention were compared with those epitopes predicted by the TEPITOPE program to bind that same MHC class II molecules. Table II lists the VP16 epitopes selected by the TEPITOPE program at a threshold level of 3%. The TEPITOPE program predicted promiscuous (epitopes that correspond to multiple MHC binding motifs) and unique (allele-specific) sequences as candidate antigens for each MHC molecule. Also listed in Table II are the specific epitopes determined by methods according to the present invention (also referred to as "TGEM"; see Example 1) scanning of the entire VP16 sequence for all six alleles.

For this analysis, sixty 20-mers (p3 to p62) were synthesized to cover the entire VP16 protein. These 60 peptides were divided up into 12 pools, with each pool consisting of 5 peptides. Each peptide pool was loaded onto MHC class II molecules and assembled into chromophore-labeled tetramers. Positive T cell binding tetramer pools were identified by flow cytometry. Individual peptides from positive T cell staining mixed-peptide tetramer pools were then used to generate unique peptide class II tetramers, and the cytometry analysis was repeated.

TABLE II

Comparison of T cell epitopes as selected by the
TEPITOPE program and those identified by the TGEM method.

| MHC allele | T cell epitopes predicted by the TEPITOPE program[a] | SEQ ID NO. | T cell epitopes identified by the TGEM approach | SEQ ID NO: |
|---|---|---|---|---|
| DRB1*0101 | 166–174 YRTVLANFC | 6 | 209–228 IADR<u>YYRETARLA</u>RVLFLHL | 37 |
| | 169–177 VLANFCSAL | 7 | | |
| | 178–186 YRYLRASVR | 8 | | |

TABLE II-continued

Comparison of T cell epitopes as selected by the TEPITOPE program and those identified by the TGEM method.

| MHC allele | T cell epitopes predicted by the TEPITOPE program[a] | SEQ ID NO. | T cell epitopes identified by the TGEM approach | SEQ ID NO: |
|---|---|---|---|---|
|  | 180–188 YLRASVRQL | 9 |  |  |
|  | 213–221 YYRETARLA[b] | 10 |  |  |
|  | 228–236 LYLFLSREI | 11 |  |  |
|  | 229–237 YLFLSREIL | 12 |  |  |
|  | 261–269 WRQLACLFQ | 13 |  |  |
|  | 271–279 LMFINGSLT | 14 |  |  |
|  | 272–280 MFINGSLTV | 15 |  |  |
|  | 323–331 LQGNQARSS | 16 |  |  |
|  | 334–342 FMLLIRAKL | 17 |  |  |
| DRB1*0401 | 166–174 YRTVLANFC | 6 | 58–69 ALFNRLLDDLGF[c] | 38 |
|  | 178–186 YRYLRASVR | 8 |  |  |
|  | 213–221 YYRETARLA | 10 | 73–92 PALCTMLDTWNEDLFSGFPT | 39 |
|  | 261–269 WRQLACLFQ | 13 |  |  |
|  | 272–280 MFINGSLTV | 15 | 233–252 SREILWAAYAEQMMRPDLFD | 40 |
|  | 274–282 INGSLTVRG | 18 | 472–484 DFEFEQMFTDAMG | 41 |
|  | 296–304 IREHLNLPL | 19 |  |  |
|  | 475–483 FEQMFTDAM | 20 |  |  |
| DRB1*0402 | 180–188 YLRASVRQL | 9 | 289–308 RLRELNHIREHLNLPLVRSA | 42 |
|  | 228–236 LYLFLSREI | 11 | 385–404 DDAPAEAGLVAPRMSFLSAG | 43 |
|  | 231–239 FLSREILWA | 21 |  |  |
|  | 261–269 WRQLACLFQ | 13 |  |  |
|  | 272–280 MFINGSLTV | 15 |  |  |
|  | 296–304 IREHLNLPL | 19 |  |  |
|  | 300–308 LNLPLVRSA | 22 |  |  |
|  | 323–331 LQGNQARSS | 16 |  |  |
|  | 333–341 YFMLLIRAK | 23 |  |  |
|  | 336–344 LLIRAKLDS | 24 |  |  |
|  | 394–402 VAPRMSFLS | 25 |  |  |
| DRB1*0404 | 166–174 YRTVLANFC | 6 | 225–244 FLHLYLFLSREILWAAYAEQ[c] | 44 |
|  | 178–186 YRYLRASVR | 8 |  |  |
|  | 228–236 LYLFLSREI | 11 | 233–252 SREILWAAYAEQMMRPDLFD | 40 |
|  | 261–269 WRQLACLFQ | 13 | 443–455 FDLEMLGDVESPS | 45 |
|  | 272–280 MFINGSLTV | 15 |  |  |
|  | 280–288 RGVPVEAR | 26 |  |  |
|  | 302–310 LPLVRSAAA | 27 |  |  |
|  | 445–453 LEMLGDVES | 28 |  |  |
|  | 475–483 FEQMFTDAM | 20 |  |  |
| DRB1*1104 | 35–43 LYATGRLSQ | 29 | 25–44 GPKNTPAAPPLYATGRLSQA | 46 |
|  | 185–193 VRQLHRQAH | 30 | 33–52 PPLYATGRLSQAQLMPSPPM[d] | 47 |
|  | 225–233 FLHLYLFLS | 31 |  |  |
|  | 231–239 FLSREILWA | 21 |  |  |
|  | 261–269 WRQLACLFQ | 13 |  |  |
|  | 272–280 MFINGSLTV | 15 |  |  |
|  | 333–341 YFMLLIRAK | 23 |  |  |
|  | 334–342 FMLLIRAKL | 17 |  |  |
|  | 336–344 LLIRAKLDS | 24 |  |  |
| DRB1*1501 | 151–159 MAQFFRGEL | 32 | 289–308 RLRELNHIREHLNLPLVRSA | 42 |
|  | 177–185 LYRYLRASV | 33 |  |  |
|  | 201–209 LREMLRTTI | 34 |  |  |
|  | 224–232 LFLHLYLFL | 35 |  |  |
|  | 226–234 LHLYLFLSR | 36 |  |  |
|  | 228–236 LYLFLSREI | 11 |  |  |
|  | 231–239 FLSREILWA | 21 |  |  |
|  | 272–280 MFINGSLTV | 15 |  |  |
|  | 296–304 IREHLNLPL | 19 |  |  |
|  | 334–342 FMLLIRAKL | 17 |  |  |
|  | 336–344 LLIRAKLDS | 24 |  |  |

[a]Epitope being selected by the TEPITOPE program was selected with a threshold level of 3%.
[b]Bold letter sequences indicate epitopes selected by the TEPITOPE program that were indentified as T cell epitopes by the TGEM approach. Underlined sequences indicated epitopes identified by the TGEM approach that were predicted by the TEPITOPE program.
[c]VP16-specific epitopes restricted by DR0401 and DR0404 have been described earlier (see Novak et al., J. Immunol. 166:6665–70 (2001)).
[d]A DR1104-restricted epitope was also identified in the 201–252 region, but was not further characterized.

As indicated in Table II, the TEPITOPE program identified major T cell epitopes for all six HLA class II alleles being examined. For DRB1*0101, DRB1*0402 and DRB1*1501, the major epitopes as identified by the TGEM approach were selected at the 1% threshold level. For DRB1*0401 and DRB1*1104, the major epitopes were selected at the 2% threshold, while for DRB1*0404 the major epitope was selected at the 3% threshold level. Epitopes such as DRB1*0401-restricted VP16 56–69 and 73–92 were not identified by TEPITOPE at a threshold value of 3%. However all of the epitopes as identified by the TGEM approach, with the exception of DRB1*0401-restricted VP16 233–252, were predicted by the TEPITOPE program at a threshold level of 10%.

Processing and presentation of antigenic peptides from a protein by MHC class II molecules is a complex process. Epitope selection depends not only on the affinity of the peptide for the MHC, but also on the availability of the peptide, which is influenced by cellular compartmentalization of the antigen and specific proteolysis of the protein. Because the TEPITOPE program predicts potential epitopes based solely on peptide affinity to the MHC pockets, it is expected that the majority of these are not likely to be presented on the cell surface as T cell epitopes. The TGEM approach, which involves exogenous loading of peptides to MHC, can be biased for peptides that bind to the MHC with high affinity and selects directly those that are recognized by CD4+ T cells. Twelve of the thirteen VP16 T cell epitopes identified by the TGEM approach were also predicted by the TEPITOPE program to be potential MHC binding peptides, thus demonstrating a high degree of biological validation in using this particular MHC peptide-binding predictive algorithm. However, it is possible that additional epitopes that have low affinity for MHC class II molecules are present, but avoid detection by both approaches.

Example 3

A T cell line that is directed against an epitope of prostate specific antigen, PSA 64–78, as been generated, establishing PSA 64–78 as an antigenic epitope. To evaluate whether PSA 64–78-loaded tetramers can be used to stain PSA specific T cells, HLA-DR0401 transgenic mice were immunized with the PSA peptide in the presence of CFA. Mice were sacrificed on day 7, T cells from the inguinale lymph nodes were isolated and stained with the DR0401/PSA 64–78 tetramers. The data show that DR0401/PSA 64–78 tetramers stain T cells from the PSA 64–78-immunized DR-4-1-IE mice. In contrast, T cells were not stained by the DR0401/PSA 64–78 tetramers in mice immunized with hemagglutinin peptide 307–319

Example 4

T cells from a human subject were screened for staining against prostate specific antigen PSA64–78, which has been established to be a T cell epitope. Blood was isolated from the subject and PBMC were prepared. Tetramers of DR0401 molecules loaded with the PSA64–78 peptide were used to stain the PBMC. The results showed the presence of T cell reactivity to this PSA epitope in the patient's blood.

Example 5

The MHC class II-restricted immune status of a human patient with autoimmune diabetes is monitored. Heparinized blood (about 15–17 ml) is diluted 1:1 with 1×PBS in a 50 ml vial. The diluted blood is underlain with 10 ml Ficoll, and then spun for 20 min at 2000 rpm. The mononuclear cells at the interface are collected and washed three times with 1×PBS. The cells are resuspended at a density of $10 \times 10^6$ cells/ml in culture medium. The culture medium is RPMI 640 supplemented with 2 mM L-glutamine, 100 µg/ml penicillin/streptomycin, 1 mM sodium pyruvate and 15% pooled human serum obtained from 20–25 healthy, non-transfused male donors.

The cells are divided into 15 ml round bottom polystyrene vials containing about $5 \times 10^6$ cells each. GAD65 peptide is added at a concentration of 10 µg/ml. The cells are then incubated at 37° C. for 10 days. On day 10, the number of cells are counted and used to prepare 48-well microtiter plates. One well per $1 \times 10^6$ cells is coated with HLA-DR monomer. The concentration of the monomer is about 5–10 µg/ml in PBS in a volume of 200 µl/well. The monomer is allowed to bind onto the plates for at least 2 hours at 37° C. The cultured cells are resuspended in culture medium containing 2 µg/ml anti-human CD28 antibody at density of $1 \times 10^6$ in 300 µl. The HLA-DR-coated microtiter plates are aspirated to remove any liquid from the wells. The wells are washed with about 400 µl of culture medium. The cultured cells are transferred into well on the monomer plates (about 300 µl/well) and incubated at 37° C. for 3 and 6 days. On day 3 (or day 6), cells are collected for analysis (e.g., by centrifugation for 5 min at 1000 rpm). The cells are resuspended in 100 µl of culture medium and divided into two flow cytometry vials. To one vial, 1 µl (final conc. 10 µg/ml) of PE-labeled HLA-DR tetramer loaded with the same GAD65 peptide as used in the specific stimulation is added. To the second vial, the same concentration of HLA-DR tetramer loaded with a control peptide (e.g., HSV or HA) is added. The vials are kept in the dark. The cells are stained for three hours at 37° C.

The vials containing the stained cells are then transferred to ice. 8–10 µl of antibodies labeled with other fluorochromes and specific for human CD4 and T-cell activation markers CD25 and CD69 are added. Control samples, single stained and unstained, are also prepared. Typically about 50–100 000 cells per one control staining is enough. The cells are stained for about 20–30 min in the dark and then washed in cold PBS one time. To determine the number of stained cells, about 200 µl FACS buffer (1×PBS and 1% FCS) is added by tapping, and the cells are analyzed for staining by flow cytometry.

Example 6

Type 1 diabetes is an autoimmune disease resulting from destruction of insulin-producing β-cells of the pancreas. Both CD4+ and CD8+ T-cells are involved in this process, which targets a number of proteins expressed in human islets. One of the best characterized of these autoantigens is glutamic acid decarboxylase (GAD65). (See, e.g., Atkinson et al., *Lancet* 339:458–59 (1992); Panina-Bordignon et al., *J. Exp. Med.* 181:1923–27 (1995).) Most Type 1 diabetes patients (70–80%) have autoantibodies against GAD65, which often appear years before the clinical onset of the disease, providing a useful predictive marker for the progression of autoimmune diabetes.

The importance of GAD65 in the development of Type 1 diabetes has also been demonstrated in diabetic NOD mice, a well known animal model of diabetes. (See, e.g., Tisch et al., *Nature* 366:72–75 (1993); Kaufman et al., *Nature* 366:69–72 (1993); Wen et al., *J. Clin. Invest.* 102:947–57 (1998); Yoon et al., *Science* 284:1183–87 (1999).) Studies on T-cell responses to GAD65 in immunized human MHC class II transgenic mice and new onset Type 1 diabetes patients have identified several immunodominant regions from GAD65 (see, e.g., Wicker et al., *J. Clin. Invest.* 98:2597–603 (1996); Patel et al., *Proc. Natl. Acad. Sci. USA* 94:8082–87 (1997); Endl et al., *J. Clin. Invest.* 99:2405–15 (1997)), one of which has recently been shown to be naturally processed. The immunodominant regions were identified by using combination of chromatography and mass spectrometry of peptides bound by HLA-DR401 molecules. (Endl et al., *J. Clin. Invest.* 99:2405–15 (1997); Nepom et al., *Proc. Natl. Acad. Sci. USA* 98:1763–68 (2001); the disclosures of which are incorporated by reference herein.) Peptides corresponding to this epitope region (GAD 554–572) elicit a T-cell response in a majority of HLA-DR4 Type 1 diabetes patients and in some at-risk subjects, indicating that this epitope represents one of the determinants recognized by CD4+ T-cells during autoimmune events associated with diabetes.

Despite the identification of at least some of immunodominant regions from GAD65, a detailed characterization of development of the T-cell response during the progression of Type 1 diabetes has been cumbersome because of lack of suitable methods to detect and isolate a small number of antigen-specific T-cells in the peripheral blood. In contrast to high affinity T-cell responses to foreign antigens, circulating autoreactive T-cells seem to be of low to moderate affinity which makes the staining of these T-cells by class II MHC multimers cumbersome. This problem can be circumvented by taking advantage of the association between tetrameric MHC class II binding and T cell activation. It has been shown both in human and mouse that upregulation of surface expression of CD4 identifies T-cells activated in an antigen-specific manner. (See Altman et al., *Science* 274: 94–96 (1996); Ridgway et al., *J Immunol.* 161:714–20 (1998); Kwok et al., *J. Immunol.* 164:4244–49 (2000); Novak et al., *J. Immunol.* 166:6665–70 (2001).) Using this upregulation of the CD4 marker, the T-cell activation profile was analyzed in newly diagnosed Type 1 diabetes patients and at-risk subjects resulting from the stimulation of peripheral blood mononuclear cells by plastic bound HLA-DR401 or 404 monomer containing a specific GAD65 peptide corresponding to the immunodominant epitope 555–567. All Type 1 diabetes patients and some at-risk subjects displayed a highly activated CD25/CD4$^{high}$+ subpopulation which contained 5–30% tetramer positive cells that were not found in normal controls. The presence of activated tetramer positive phenotype correlated with Type 1 diabetes and possibly reflects the progression of the disease prior the clinical onset.

Methods

Subjects.

Blood samples from patients with Type 1 diabetes (ages 14–25 years) were obtained 4–8 weeks post-onset. At-risk subjects were positive for two or more autoantibodies (GAD65, IA-2 and IAA), except one who had low level of IAA and impaired glucose tolerance test. All patients except one (7929) were being treated for diabetes at Virginia Mason Medical Center Section of Endocrinology and the at-risk subjects were participants of prediabetes screening program at the Virginia Mason Research Center. Healthy blood donors were recruited from the hospital/research center staff. Only subjects positive for DR401 or DR404 were included in this study.

Preparation of HLA-DR401 and DR404 Monomers and Tetramers.

The construction of the expression vectors for generation of soluble DRA*0101/DRB1*0401 has been described previously. (Novak et al., *J. Clin. Invest.* 104:R63–R67 (1999); the disclosure of which is incorporated by reference herein.) Briefly, a site-specific biotinylation sequence was added to the 3' end of the DRB1*0401 or DR404 leucine zipper cassette, and chimeric cDNA was subcloned into Cu-inducible Drosophila expression vector. DR-A and DR-B expression vectors were co-transfected into Schneider S-2 cells, purified, concentrated and biotinylated. Specific peptide was loaded for 48–72 hours, and tetramers were formed by incubating MHC class II molecules with PE-labeled streptavidin (Biosource International, Camarillo, Calif.).

Isolation and Stimulation of PBMC.

Peripheral blood mononuclear cells (PBMC) were separated from heparinized blood by gradient centrifugation (Lymphoprep, Nycomed, Oslo, Norway). Cells were resuspended in RPMI 1640 (Gibco/BRL, Rockville, Md.) supplemented with 2 mM L-glutamine, 1 mM sodium pyruvate, 100 µg/ml penicillin/streptomycin and 15% v/v pooled human serum, and cultured in the presence of a GAD65 555–567 (557I) (NFIRMVISNPAAT; SEQ ID NO: 48) peptide at concentration of 10 µg/ml. From some samples a control culture was set up with a MBP 84–102 (NPVVH-FFKNIVTPRTPPP; SEQ ID NO: 49) peptide which binds well to DR401 and 404. On day 6–10, the cells were transferred at a density of 4×10$^6$/ml onto 48-well plate that had been coated with DR401 or DR404 monomer in 1×PBS for 2 hours at 37° C. The MHC class II monomer contained the same peptide as used in the primary culture. One µg/ml anti-CD28 antibody (BD/Pharmingen, San Jose, Calif.) was added in the culture.

Identification of T-cell Activation and Tetramer Staining by Flow Cytometry.

On day 3, the stimulated cells were stained by 10 µg/ml of PE-labeled HLA-DR401 or 404 tetramer for 3 hours at 37° C., and subsequently with fluorochrome-labelled anti-CD25 and anti-CD4 (BD/Pharmingen, San Jose, Calif.) for 30 minutes on ice. Cells were then washed with PBS containing 1% FBS and analyzed using Becton-Dickinson FACSCalibur flow cytometer. The calibration was performed by using cells stained by single fluorochrome anti-CD4. Data analysis was performed by using WinMdi (Stanford University) and CellQuest (Becton Dickinson) softwares.

Fluorescent Single Cell Sorting, T-cell Cloning and Proliferation Assay.

The top 1% of the CD25/CD4$^{high}$ cells from an at-risk subject (6212) were single-cell sorted into 96-well plates using a FACS Vantage cell sorter (Becton Dickinson). Clones were expanded for 10 days by stimulation with irradiated unmatched PBMC (1.5×10$^5$/well), 5 µg/ml PHA and 10 U/ml IL-2. Subsequently, the cells were stimulated by HLA-DR404+ PBMC pulsed with 10 µg/ml of GAD65 557I peptide and 10 units/ml IL-2, and on day 7 selected by growth for further expansion. The resting T-cells were tested in several experiments for proliferation by stimulating 2×10$^4$ T-cells by thawn irradiated autologous PBMC (5–10×10$^4$/well) with and without a specific peptide. Both GAD65 557I and wild type 555–567 peptides (0.1–10 µg/ml) were tested for the induction of proliferation of the T-cells clones. $^3$H-thymidine incorporation was measured at 72 hours.

Results

T-cells from Type 1 Diabetes Patients Stimulated by GAD65 557I Peptide Show CD25/CD4$^{high}$ Phenotype.

PBMC from four new onset Type 1 diabetes patients were stimulated with 10 µg/ml GAD65 557I peptide for 6–10 days. This peptide, NFIRMVISNPAAT, has a F→I (phenylalanine to isoleucine) substitution at position 557, which has been shown to enhance agonist activity for proliferation and cytokine release from DR4 restricted T-cells. Following the primary PBMC culture, the cells were stimulated with plastic-bound DR401 or DR404 monomer containing GAD65 557I or irrelevant peptide and soluble anti-CD28 antibody (1 µg/ml). On day 3, the cells were stained by fluorochrome conjugated specific and control tetramers, anti-CD25 and anti-CD4 surface markers and analyzed by flow cytometry. All four patients had a highly activated T-cell subset expressing a CD25/CD4$^{high}$ phenotype. In a recent study, this T-cell subset had been demonstrated to include freshly activated cells that are antigen-specific (Kwok et al., *J. Immunol.* 164:4244–49 (2000); Novak et al., *Int. Immunol.* 13:799–806 (2001)). In normal subjects this activation phenotype is not present.

Correlation between TNFα Production and GAD65 557I Induced Activation of CD4 T-Cells.

Culture supernatants for cytokine analysis were collected at 48 hours post-secondary stimulation by plate-bound class II MHC monomer. The number of T-cells with CD4$^{high}$ phenotype among all CD4/CD25 positive cells correlated with the level of TNFα production in samples from Type 1 diabetes patients. Stimulation by an irrelevant HLA-DR4 monomer containing HSV p61 peptide or stimulation by soluble anti-CD28 only did not induce either CD4$^{high}$ expression or TNFα production. Lack of T-cell activation and TNFα production was evident in normal subjects.

The T-cell Activation Profile is Heterogeneous in At-Risk Subjects.

GAD65 epitope specific T-cell activation was also investigated in five at-risk subjects who were either HLA-DRB1*0401 (5574, 7657, 7878, 6827) or DRB1*0404 (6212). Four (6212, 5574, 7657, 7878) were positive for two or more autoantibodies. One subject (6827) was positive for low levels insulin autoantibodies and had impaired glucose tolerance. The subject 6212 had a distinct subset of CD25/CD4$^{high}$ positive T-cells, as observed in all patients with Type 1 diabetes. Subjects 5574 and 7657 had a high number of CD25+ T-cells but they are CD4$_{low}$ phenotype. Subject 6827 displayed a similar frequency of CD25/CD4+ T-cells as the subject 6212, but they are CD25/CD4$_{low}$. Two blood samples from the at-risk subject 7878 were also examined. One sample was drawn five months before the subsequent one. The activation profiles showed a dramatic difference between these two time-points. The T-cells from the first sample show hardly any activation when stimulated with the GAD65 557I peptide in contrast to the T-cells obtained a few months later which express a distinct CD25/CD4$^{high}$ phenotype. This difference in the GAD65 specific T-cell response indicates progression to Type 1 diabetes.

GAD65 Specific Cells are Identified by Tetramer Staining in the CD25/CD4$^{high}$ Population.

HLA-DR4 GAD tetramers were used to stain cells gated on CD25/CD4$^{high}$ markers. In one example, tetramer staining of the sample from Type 1 diabetes patient 7810 was analyzed. One third of the cells expressing CD25/CD4$^{high}$ phenotype stained with the specific GAD65 tetramer. Binding to HSVp61-control tetramer was 1.5%. In a second example, tetramer staining in at-risk subject 6212, the gating criteria were the same as in the previous patient. 8.6% of the CD25/CD4$^{high}$ cells bound the GAD65 tetramer. The slightly higher background staining 3.2% could be a property of the control tetramer HSVp61-DR404 since the same level of background staining was seen also in other DR404+ samples. In a third example, the lack of tetramer staining in an at-risk subject 7657 (who had an increased number of CD25/CD4low+cells) was observed. Since this subject lacked the subset of CD4$^{high}$ cells, the gating was set on the top 25% of CD25/CD4 positive cells, but no tetramer positive cells were detected in this CD25/CD4 low population. The lack of tetramer staining in CD25/CD4$_{low}$ cell population was observed also in Type 1 diabetes patients. Overall, these findings indicate that CD4+ T-cells that are able to bind GAD tetramers reside in the highly activated antigen-specific cell population characterized by the simultaneous high level of expression of CD25 and CD4.

Correlation of CD25/CD4$^{high}$ Phenotype, Tetramer Staining and Type 1 Diabetes.

All four new onset diabetic patients had a highly activated CD25/CD4$^{high}$ cell population which was induced upon stimulation by GAD65 557I peptide, and 5–33% of these cells also had ability to bind a GAD65 tetramer. The same activation profile, including positive tetramer staining, was also observed in two at-risk subjects. In one of these subjects, the activated phenotype of CD4+ T-cells was not present in an earlier sample, consistent with an emerging T-cell response towards this particular epitope. Heterogeneity in the GAD65 specific T-cell response among at-risk individuals in terms of the expression of activation markers and tetramer staining is suggestive of the correlation. Activation of T-cells to the GAD peptide indicated either by CD25 or CD4$^{high}$ expression was not detected in normal subjects. Also, PBMC from Type 1 diabetes patients or at-risk subjects were stimulated by irrelevant peptide (MBP) in the primary culture, and then exposed to control plate-bound empty class II MHC, no activation or tetramer staining was observed.

CD25/CD4$^{high}$ Sorted Cells are GAD65 555–567 Specific.

Specificity of the T-cell activation profile was examined in a more detailed fashion, using single-cell sorting of the CD25/CD4$^{high}$ cells from an at-risk subject 6212 positive for HLA-DR404/DR405, using flow cytometry to select the top 1% of the CD4+ staining intensity. Seven clones from 140 tested proliferated consistently in the presence of GAD65 557I peptide in replicate experiments. The T-cell proliferation in the presence of peptide was dose-dependent and the clones similarly responded to wild type peptide GAD65 555–567 with a lower level of proliferation.

Discussion

In this study, the use of soluble multimeric MHC class II complexes has enabled the identification of antigen-specific T-cells in Type 1 diabetes patients and some at-risk subjects. The methods take advantage of the appearance of highly activated T-cells expressing a CD25/CD4$^{high}$ phenotype induced by plate-bound class II MHC monomer containing the GAD65 peptide. This strategy to study antigen-specific T-cell response in an autoimmune disease is designed to overcome some of the difficulties associated with low precursor frequency and low level of staining in the total population of CD4+ T cells, which often is not significantly above the background staining. These methods have allowed the demonstration in Type 1 diabetes patients, and in some at-risk subjects, HLA-DR4 monomer induced activation profile characterized by upregulation of CD4 on GAD65 specific T-cells. Almost all T-cells that stain with the specific tetramer reside in this population and since this activation profile is not present in normal subjects it provides a useful tool for analysis of the T cell response in autoimmune diabetes.

The correlation between T-cell activation, CD25/CD4$^{high}$ phenotype and tetramer staining was significant in subjects that have Type 1 diabetes or have signs of diabetes-associated autoimmunity. The utilization of methods according to the present invention in the detection of autoreactive T-cells in Type 1 diabetes patients and at-risk subjects is useful to gain insights into mechanisms of molecular basis of autoimmunity. The phenotyping of T-cells provides useful markers for progression of immune-mediated B-cell reactivity and can be utilized in clinical trials to evaluate the efficacy of the immunomodulatory therapies targeting intervention/prevention of Type 1 diabetes.

The previous examples are provided to illustrate but not to limit the scope of the claimed inventions. Other variants of the inventions will be readily apparent to those of ordinary skill in the art and encompassed by the appended claims. All publications, patents, patent applications and other references cited herein are hereby incorporated by reference.

---

What is claimed is:

1. A method for identifying an MHC class II epitope of a predetermined polypeptide antigen, comprising;
   preparing a library of at least two peptide pools, each peptide pool comprising at least two peptides, the peptides comprising a fragment of the predetermined polypeptide antigen and sharing a region of overlapping amino acid sequence identity with at least one other peptide in the library;
   forming pools of MHC class II/peptide tetramers from the pools of peptides and soluble human MHC class II molecules, each MHC class II/peptide tetramer comprising four MHC class II molecule/peptide pairs, wherein the peptides are bound to the MHC class II molecules, said forming of MHC class II/peptide tetramers comprising loading the human MHC class II molecules with the peptide pools;
   contacting the pools of MHC class II/peptide tetramers with human T cells;
   identifying at least one pool of MHC class II/peptide tetramers that binds to the T cells; and
   contacting T cells with MHC class II/peptide tetramers Conned with individual peptides from the pool of MHC class II/peptide tetramers that binds to the T cells to identify at least one epitope in the peptide pool.

2. The method of claim 1, wherein the identifying is by fluorescence activated cell sorting, T cell proliferation assay or cytokine secretion capture assay.

3. The method of claim 1, wherein the T cells are peripheral blood mononuclear cells.

4. The method of claim 1, further comprising confirming the identification of the pool of MHC class II/peptide tetramers that bind to the T cells by T cell proliferation assay or cytokine secretion capture assay.

5. The method of claim 4, wherein the cytokine secretion capture assay detects IFN gamma production.

6. The method of claim 1, wherein the soluble MHC Class II molecules are loaded by contacting the soluble MHC class II molecules with about a 10 to about a 25 fold molar excess of the peptide pools.

7. The method of claim 1, wherein the peptides are about 10 to about 20 amino acids in length.

8. The method of claim 1, wherein each peptide pool comprises between about 3 to about 8 different peptides.

9. The method of claim 8, wherein each peptide pool has about 5 different peptides.

10. The method of claim 1, wherein the soluble human MHC class II molecules comprise α subunits and β subunits, the α subunits being HLA-DPα, HLA-DQα or HLA-DRα, and the β subunits being HLA-DPβ, HLA-DQβ or HLA-DRβ.

11. The method of claim 1, wherein the soluble human MHC class II molecules comprise separate α and β subunits, each subunit having a leucine zipper domain and a conformationally flexible linker region.

12. The method of claim 1, wherein the soluble human MHC class II molecules further comprise a ligand, and the MHC class II tetramers are formed by interaction of the ligand with a polyvalent binding partner.

13. The method of claim 12, wherein the polyvalent binding partner is streptavidin.

14. The method of claim 12, wherein the binding partner is labeled.

15. The method of claim 14, wherein the label is a radioactive molecule, a luminescent molecule, a fluorescent molecule, an enzyme, or biotin.

16. The method of claim 14, wherein the label is attached to the binding partner by a spacer.

* * * * *